United States Patent
Raimundo et al.

(10) Patent No.: US 10,940,425 B2
(45) Date of Patent: Mar. 9, 2021

(54) COMPOUNDS FOR THE DETECTION, CAPTURE AND/OR SEPARATION OF POLLUTING GASES

(71) Applicants: Centre National de la Recherche Scientique—CNRS-, Paris (FR); Université d'Aix-Marseille, Marseilles (FR)

(72) Inventors: Jean-Manuel Raimundo, Carnoux en Provence (FR); Vinicius Demétrio da Silva, Aix en Provence (FR); Philip Leslie Llewellyn, Marseilles (FR); Julien Rodriguez, Septemes les Vallons (FR); Olivier Yves Claude Siri, Belcodène (FR)

(73) Assignees: Centre National de la Recherche Scientifique, Paris (FR); Universite d'Aix-Marseille, Marseilles (FR)

( * ) Notice: Subject to any disclaimer, the term of this patent is extended or adjusted under 35 U.S.C. 154(b) by 19 days.

(21) Appl. No.: 16/064,797

(22) PCT Filed: Dec. 23, 2016

(86) PCT No.: PCT/EP2016/082568
§ 371 (c)(1),
(2) Date: Jun. 21, 2018

(87) PCT Pub. No.: WO2017/109178
PCT Pub. Date: Jun. 29, 2017

(65) Prior Publication Data
US 2019/0001252 A1   Jan. 3, 2019

(30) Foreign Application Priority Data
Dec. 24, 2015   (EP) .................................. 15307147.7

(51) Int. Cl.
| | |
|---|---|
| *B01D 53/02* | (2006.01) |
| *C07C 317/36* | (2006.01) |
| *C07C 323/65* | (2006.01) |
| *C07D 213/70* | (2006.01) |
| *C07D 281/00* | (2006.01) |
| *C07D 225/04* | (2006.01) |
| *C07D 341/00* | (2006.01) |
| *B01J 20/22* | (2006.01) |
| *C07D 257/10* | (2006.01) |

(Continued)

(52) U.S. Cl.
CPC .............. *B01D 53/02* (2013.01); *B01J 20/22* (2013.01); *C07C 317/36* (2013.01); *C07C 323/65* (2013.01); *C07D 213/70* (2013.01); *C07D 225/04* (2013.01); *C07D 257/10* (2013.01); *C07D 281/00* (2013.01); *C07D 285/00* (2013.01); *C07D 341/00* (2013.01);

*G01N 33/0004* (2013.01); *B01D 2253/20* (2013.01); *B01D 2257/504* (2013.01)

(58) Field of Classification Search
CPC ............................. B01D 53/02; C07D 281/00
See application file for complete search history.

(56) References Cited

U.S. PATENT DOCUMENTS 2,954,412 A * 9/1960 Horst-Dieter ........... C07C 15/16
585/422

FOREIGN PATENT DOCUMENTS

GB           961305 A        6/1964

OTHER PUBLICATIONS

"Highly CO2 Selective Organic Molecular Cages: What Determines the CO2 Selectivity" Yunghua Jin, Breat A Voss Athena Jin Hai Long Richard D. Noble and Wei Zhang. Journal of the American Chemical Society 133 6650-6658 (Year: 2011).*
Conostruction and Multiple Exterior Surface Functionalization of Giant Molecular Cages European Journal of Organic Chemistry pp. 7896-7905 Muhammad Moazzam Naseer DeXianWang Lian Zhao and Mei Xian Wang (Year: 2014).*
Synthesis and Functionalization of HeteroAtom Bridged Bicyclocalixaromatic Large Molecular Triangular Prims with Eelectron Rich and Deficient Aromatic Interiors; Muhammad Moazzam Naseer, De Xian Wang Liang Zhao Zhi Tang Huang and Mei Xian Wang ACS Journad of Organic Chemistry pp. 1804-1813 (Year: 2011).*

(Continued)

*Primary Examiner* — Noble E Jarrell
(74) *Attorney, Agent, or Firm* — Morgan, Lewis & Bockius LLP

(57) ABSTRACT

A subject of the present invention is the use of a compound having the general formula (I): (I) wherein V, W, $X_4$, $X_5$, $X_6$, $X_7$, $X'_4$, $X'_5$, $X'_6$, $X'_7$, Y, Y', $R_3$, $R'_3$, $R_4$ and $R'_4$ are as defined in any one of claims 1 to 11, for the detection, capture and/or separation of polluting gases, in particular those selected from the group comprising carbon dioxide, methane, sulfur dioxide, nitrogen oxides, carbon monoxide, linear hydrocarbons, linear mono-olefins and their mixtures, and preferably carbon dioxide. Another subject of the invention is a compound of formula (I) wherein V, W, $X_4$, $X_5$, $X_6$, $X_7$, $X'_4$, $X'_5$, $X'_6$, $X'_7$, Y, Y', $R_3$, $R'_3$, $R_4$ and $R'_4$ are as defined in any one of claims 12 to 21.

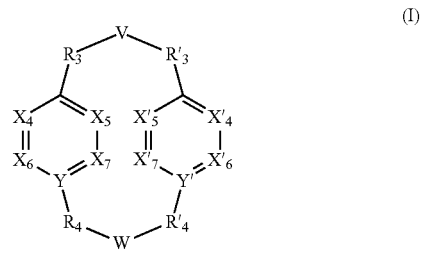

22 Claims, 3 Drawing Sheets

(51) Int. Cl.
*C07D 285/00* (2006.01)
*G01N 33/00* (2006.01)

(56) References Cited

OTHER PUBLICATIONS

Montaudo et al., "Conjugative and steric factors affecting the conformational preference of some aromatic sulfides," Journal of Organic Chemistry, 37: 504-505 (1972).
Bock et al., "Chapman rearrangements. Synthesis of aromatic N, N'-diaryldiamines with o,o'-positioned carboxyl groups," Chemische Berichte, 100: 2870-2884 (1967).
Livingston et al., "Action of sulfinates on 1:5-Dichloro-2:4-dinitrobenzene," Journal of the Chemical Society, 246-249 (1937).
Touil et al., "Unprecedented N(H)-bridged tetraaza[1.1.1.1]m,p,m,p-cyclophanes," Tetrahedron, 66: 4377-4382 (2010).
Nussbaum et al., "Efficient Electronic Communication of Two Ruthenium Centers through a Rigid Ditopic N-Heterocyclic Carbene Linker," Chemistry—A European Journal, 19: 17517-17527 (2013).
Stuhr-Hansen et al., "Sparing the ortho-position in nucleophilic aromatic substitution-specific displacement of the 4-SePh group in 2,4-bis(phenylseleno)nitrobenzene," Heteroatom Chemistry, 20: 101-108 (2009).
International Search Report issued in corresponding International Patent Application No. PCT/EP2016/082568 dated May 12, 2017.
Written Opinion issued in corresponding International Patent Application No. PCT/EP2016/082568 dated May 12, 2017.
Jacobson, "Review of solutions to global warming, air pollution, and energy security," Energy & Environmental Science, 2: 148-173 (2009).
Hou et al., "Understanding the Adsorption Mechanism of C2H2, CO2, and CH4 in Isostructural Metal-Organic Frameworks with Coordinatively Unsaturated Metal Sites," Journal of Physical Chemistry, 117: 2824-2834 (2013).
Wiersum et al., "Experimental Screening of Porous Materials for High Pressure Gas Adsorption and Evaluation in Gas Separations: Application to MOFs (MIL-100 and CAU-10)," ACS Combinatorial Science, 15: 111-119 (2013).
D'Alessandro et al., "Carbon Dioxide Capture: Prospects for New Materials," Angewandte Chemie, 49: 6058-6082 (2010).
Metz et al., "Intergovernmental Panel on Climate Change: Carbon Dioxide Capture and Storage," (2005).
Stern, "Stem Review: The Economics of Climate Change," (2006).

* cited by examiner

COMPOUNDS FOR THE DETECTION, CAPTURE AND/OR SEPARATION OF POLLUTING GASES

RELATED PATENT APPLICATIONS

The present application is filed pursuant to 35 U.S.C. § 371 as a U.S. National Phase Application of International Patent Application No. PCT/EP2016/082568, which was filed on Dec. 23, 2016, claiming the benefit of priority to European Patent Application No. EP 15307147.7 filed on Dec. 24, 2015. The content of each of the aforementioned Patent Applications is incorporated herein by reference in its entirety.

FIELD OF THE INVENTION

The present invention relates to new compounds and their use for the detection, capture and/or separation of polluting gases, in particular carbon dioxide.

BACKGROUND OF THE INVENTION

The escalating level of atmospheric carbon dioxide is one of the most pressing environmental concerns of our age. The prospect of a worsening climatic situation due to global warming is a subject of widespread public concern, with annual global emissions of $CO_2$ having escalated by approximately 80% between 1970 and 2004[1]. This drastic rise has been attributed to an increasing dependence on the combustion of fossil fuels (coal, petroleum and natural gas), which account for 86% of anthropogenic greenhouse gas emissions, the remainder arising from land use change (primarily deforestation) and chemical processing[2].

The urgent need for strategies to reduce global atmospheric concentrations of greenhouse gases has prompted action from national and international governments and industries, and a number of high-profile collaborative programs have been established including the Intergovernmental Panel on Climate Change, the United Nations Framework Commission on Climate Change, and the Global Climate Change Initiative. The capture and sequestration of carbon dioxide—the predominant greenhouse gas—is a central strategy in these initiatives, as it offers the opportunity to meet increasing demands for fossil fuel energy in the short— to medium-term, whilst reducing the associated greenhouse gas emissions in line with global targets[3].

Carbon capture and storage (CCS) from large point sources such as power plants is one option for reducing anthropogenic $CO_2$ emissions; however, currently the capture alone will increase the energy requirements of a plant by 25-40%. The capture methods, which have the greatest likelihood of reducing $CO_2$ emissions to the atmosphere, are post-combustion (predominantly $CO_2/N_2$ separation), pre-combustion ($CO_2/H_2$) capture, and natural gas sweetening ($CO_2/CH_4$). The key factor, which underlies significant advancements, lies in improved materials that perform the separations. In this regard, the most recent developments and emerging concepts in $CO_2$ separations are solvent absorption, chemical and physical adsorption, and membranes, amongst others, with particular attention on progress in the burgeoning field of metal-organic frameworks.

However, despite the numerous challenges surrounding $CO_2$ capture, and the various political, regulatory and economic drivers which will ultimately dictate the time-to-deployment for new CSS schemes, there is still a need in solving the $CO_2$ capture problem[4]. In fact, the problem of the $CO_2$ capture is regarded as one of the grand challenges for the 21$^{st}$ century[3].

SUMMARY OF THE INVENTION

One of the objectives of the invention is thus to find novel means for the depollution of the environment.

More particularly, one of the objectives of the invention is to find novel means to reduce the concentration of polluting agents, which are present in the air and/or in biological areas, said polluting agents being in particular polluting gases.

The invention relates to a new class of semi-rigid mesoporous and non-planar molecules having variable cavities bearing functional chemical groups, which are able to interact specifically with gaseous or non-gaseous pollutants.

The molecules of the invention are of interest in environmental and biological areas for the detection, separation and/or sequestration of pollutants.

DETAILED DESCRIPTION OF THE INVENTION

Use

A subject of the invention is the use of a compound having the general formula (I):

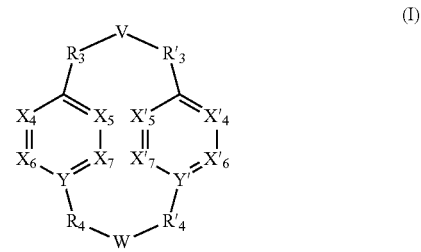

wherein
V represents:

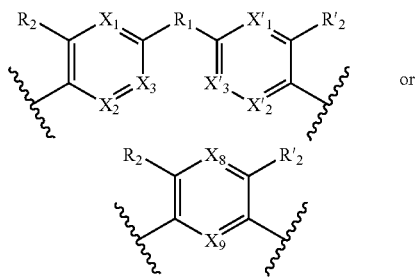

W has the same meaning as V or W is absent, and when W is absent then $R_4$ and $R'_4$ are also absent, $X_1, X_2, X_3, X'_1, X'_2, X'_3, X_4, X_5, X_6, X_7, X'_4, X'_5, X'_6, X'_7, X_8$ and $X_9$ are each independently N or a CH group, when W has the same meaning as V, then Y and Y' are each a carbon atom, when W is absent, then Y and Y' are each independently N or a CR group, with R representing H, $R_a$, $NR_aR_b$, $OR_a$, $SR_a$, $CO_2R_a$, $COR_a$, $CONHR_a$, $CONR_aR_b$, $NHCOR_a$, $SO_2R_a$, $SO_2NHR_a$, $SO_2NR_aR_b$, $PR_aR_b$, $P(O)R_aR_b$, $P(O)(OR_a)(OR_b)$, $CH_2PO(OR_a)(OR_b)$, COCH₂COR_a, CSOR_a, CSR_a, CSNHR_a, CSNR_aR_b, NHCSR_a, P(S)R_aR_b, CSCH₂CSR_a, NHCONHR_a, NHCSNHR_a or a five or six-membered aromatic or heteroaromatic compound chosen from benzene, pyridine, diazine, triazine, tetrazine, pyrrole, thiophene, furan, azole, triazole or tetrazole, with $R_a$ and $R_b$ being each independently H, OH; an alkyl radical having from 1 to 10 carbon atoms (alkyl $C_1$-$C_{10}$); a five or six-membered carbocycle chosen from cyclohexane, piperidine, piperazine, tetrahydrothiophene, tetrahydropyrrole or dihydroazole; or an aromatic or heteroaromatic compound chosen from pyridine, diazine, triazine, tetrazine, pyrrole, thiophene, furan, azole, triazole, tetrazole, benzoazole, benzotriazole or indole, $R_1$ represents O, S, $SO_2$, SO, CO, a $NR_a$, $SiR_aR_b$, $SnR_aR_b$, $BR_a$ or a $PR_a$ group, $R_a$ and $R_b$ being as defined above, $R_2$ and $R'_2$ are each independently $COOR_a$, $NO_2$, $CONR_aR_b$, $SO_2R_a$, $SO_3H$, $OSO_3H$, $COR_a$, $PO_3H_2$, $OPO_3H_2$ or CN, $R_a$ and $R_b$ being as defined above, $R_3$, $R'_3$, $R_4$ and $R'_4$ are each independently S, $NR_a$, P, Se or Te, $R_a$ being as defined above, for the detection, capture and/or separation of polluting gases, in particular those selected from the group comprising carbon dioxide, methane, sulfur dioxide, nitrogen oxides, carbon monoxide, linear hydrocarbons, linear mono-olefins and their mixtures, and preferably carbon dioxide.

When W is present then compounds of formula (I) are cyclic compounds.

According to one embodiment of the invention, in compound of formula (I) as defined above, used for the detection, capture and/or separation of polluting gases:

V represents:

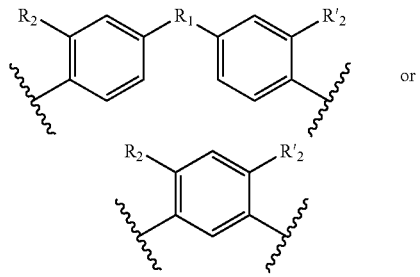

$X_4$, $X_5$, $X_6$, $X_7$, $X'_4$, $X'_5$, $X'_6$ and $X'_7$ are each independently N or CH, when W has the same meaning as V, then Y and Y' are each a carbon atom, when W is absent, then Y and Y' are each independently N or a CR group, R being H, $NR_aR_b$, $CO_2R_a$, $P(O)(OR_a)(OR_b)$, $CH_2PO(OR_a)(OR_b)$, $R_1$ represents S, $SO_2$, $NR_a$ or O, $R_2$ and $R'_2$ are each independently $NO_2$, $COOR_a$, $COR_a$ or $CONR_aR_b$, $R_3$, $R'_3$, $R_4$ and $R'_4$ are each independently S or $NR_a$, with $R_a$ and $R_b$ are each independently H or an alkyl $C_1$-$C_{10}$.

According to a particular embodiment of the invention, in compound of formula (I), $X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $X_8$ and $X_9$ are each CH.

According to another embodiment of the invention, in compounds of formula (I) as defined above, used for the detection, capture and/or separation of polluting gases:

W, $R_4$ and $R'_4$ are absent,

V represents:

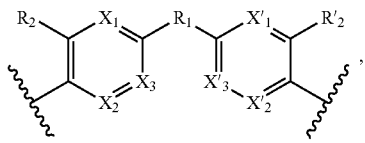

$X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $R_1$, $R_2$, $R'_2$, $R_3$ and $R'_3$ are as defined above, Y and Y' are as defined above when W is absent.

Said compounds can thus be represented by a general formula (I-1), which is more specific than (I):

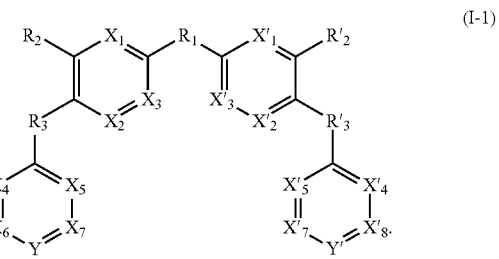

When:
$X_1$=$X_2$=$X_3$=$X'_1$=$X'_2$=$X'_3$,
$X_4$=$X_5$=$X_6$=$X_7$=$X'_4$=$X'_5$=$X'_6$=$X'_7$,
$R_2$=$R'_2$,
$R_3$=$R'_3$ and,
Y=Y', then compounds of formula (I-1) are symmetrical compounds.

As an example of compound of general formula (I), and more particularly of formula (I-1), used for the detection, capture and/or separation of polluting gases, one can cited one of those selected from the group consisting of compounds of formula (I) wherein:

Y=Y'=$CNH_2$, $R_1$=$SO_2$, $R_2$=$R'_2$=$NO_2$ and $R_3$=$R'_3$=S (1),
Y=Y'=$CNH_2$, $R_1$=$SO_2$, $R_2$=$R'_2$=$NO_2$ and $R_3$=$R'_3$=NH (2),
Y=Y'=N, $R_1$=$SO_2$, $R_2$=$R'_2$=$NO_2$ and $R_3$=$R'_3$=S (3),
Y=Y'=N, $R_1$=$SO_2$, $R_2$=$R'_2$=$NO_2$ and $R_3$=$R'_3$=NH (4),
Y=Y'=N, $R_1$=$SO_2$, $R_2$=$R'_2$=$COOR_a$ and $R_3$=$R'_3$=NH (5),
Y=Y'=N, $R_1$=$SO_2$, $R_2$=$R'_2$=$COOR_a$ and $R_3$=$R'_3$=S (6),
Y=Y'=N, $R_1$=S, $R_2$=$R'_2$=$COOR_a$ and $R_3$=$R'_3$=S (7),
Y=Y'=N, $R_1$=S, $R_2$=$R'_2$=$COOR_a$ and $R_3$=$R'_3$=NH (8),
Y=Y'=$CNH_2$, $R_1$=S, $R_2$=$R'_2$=$COOR_a$ and $R_3$=$R'_3$=NH (9),
Y=Y'=$CNH_2$, $R_1$=S, $R_2$=$R'_2$=$COOR_a$ and $R_3$=$R'_3$=S (10),
Y=Y'=$CNH_2$, $R_1$=S, $R_2$=$R'_2$=$CONR_aR_b$ and $R_3$=$R'_3$=S (11), Y=Y'=CNH$_2$, R$_1$=S, R$_2$=R'$_2$=CONR$_a$R$_b$ and R$_3$=R'$_3$=NH (12), Y=Y'=CNH$_2$, R$_1$=SO$_2$, R$_2$=R'$_2$=CONR$_a$R$_b$ and R$_3$=R'$_3$=NH (13), Y=Y'=CNH$_2$, R$_1$=SO$_2$, R$_2$=R'$_2$=CONR$_a$R$_b$ and R$_3$=R'$_3$=S (14), Y=Y'=N, R$_1$=SO$_2$, R$_2$=R'$_2$=CONR$_a$R$_b$ and R$_3$=R'$_3$=S (15), Y=Y'=N, R$_1$=SO$_2$, R$_2$=R'$_2$=CONR$_a$R$_b$ and R$_3$=R'$_3$=NH (16), Y=Y'=CCOOH, R$_1$=SO$_2$, R$_2$=R'$_2$=NO$_2$ and R$_3$=R'$_3$=S (17), Y=Y'=CCH$_2$PO(OC$_2$H$_5$)$_2$, R$_1$=SO$_2$, R$_2$=R'$_2$=NO$_2$ and R$_3$=R'$_3$=NH (18), and in each compound (1) to (18):

X$_1$=X$_2$=X$_3$=X'$_1$=X'$_2$=X'$_3$=X$_4$=X$_5$=X$_6$=X=X'$_4$=X'$_5$=X'$_6$=X'$_7$=CH,

R$_a$ and R$_b$ are each independently H or an alkyl C$_1$-C$_{10}$.

Compounds (1) to (18) of formula (I-1) are represented in Table 1 below.

Table 1:

TABLE 1

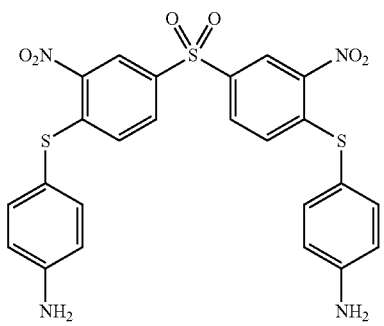 [SMILES: Nc1ccc(Sc2ccc(S(=O)(=O)c3ccc(Sc4ccc(N)cc4)c([N+](=O)[O-])c3)cc2[N+](=O)[O-])cc1]
(1)

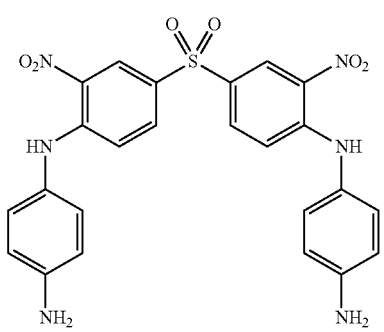 [SMILES: Nc1ccc(Nc2ccc(S(=O)(=O)c3ccc(Nc4ccc(N)cc4)c([N+](=O)[O-])c3)cc2[N+](=O)[O-])cc1]
(2)

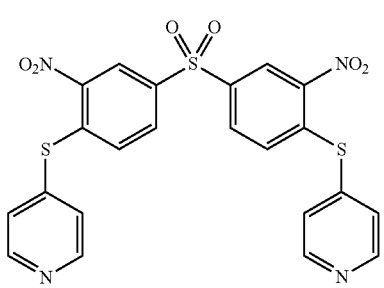 [SMILES: O=[N+]([O-])c1cc(S(=O)(=O)c2ccc(Sc3ccncc3)c([N+](=O)[O-])c2)ccc1Sc1ccncc1]
(3)

TABLE 1-continued

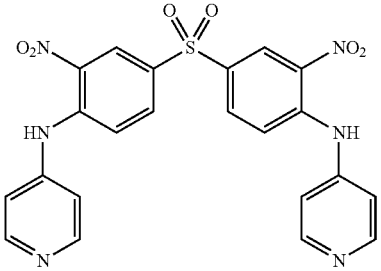 [SMILES: O=[N+]([O-])c1cc(S(=O)(=O)c2ccc(Nc3ccncc3)c([N+](=O)[O-])c2)ccc1Nc1ccncc1]
(4)

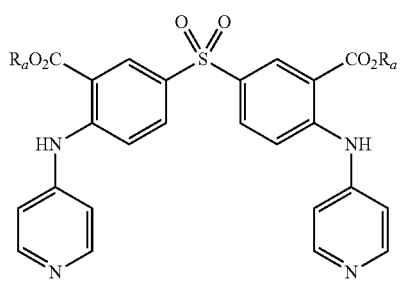
(5)

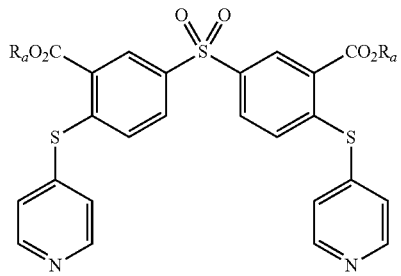
(6)

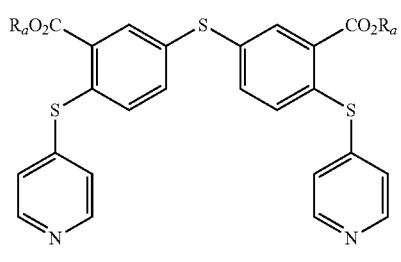
(7)

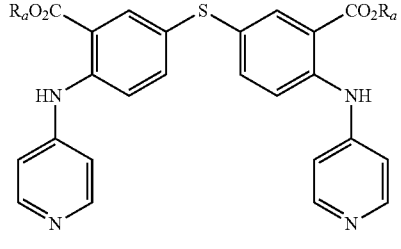
(8)

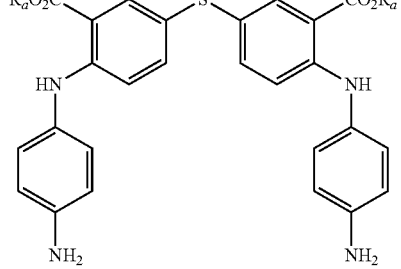
(9)

TABLE 1-continued
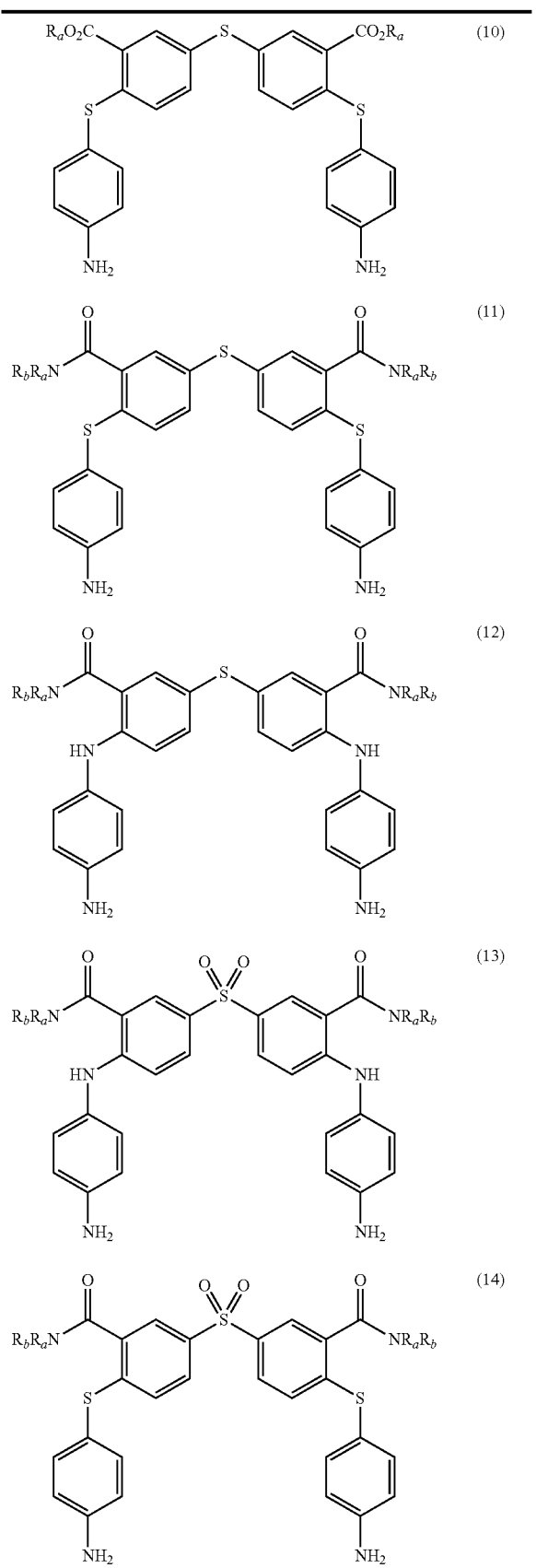
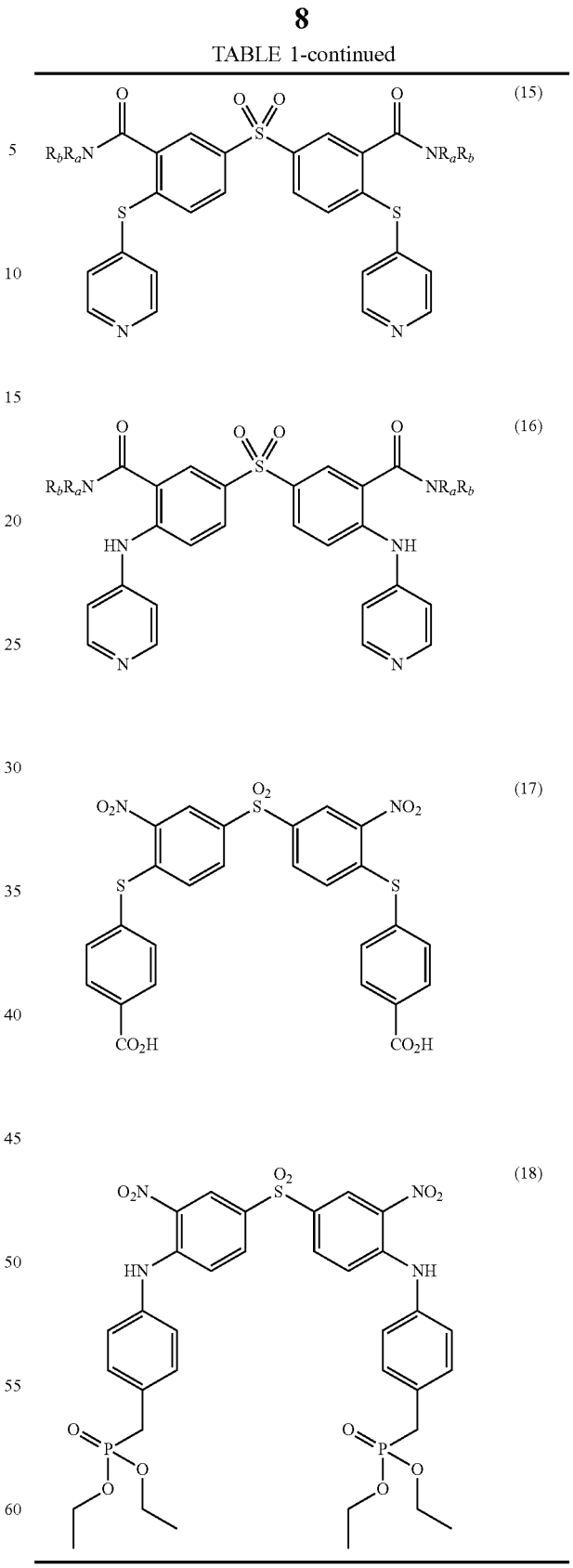
According to a particular embodiment of the invention, compounds (1) and (2) responding to general formula (I-1) can be cited for their use for the detection, capture and/or separation of polluting gases.

According to another embodiment of the invention, in compounds of formula (I) as defined above, used for the detection, capture and/or separation of polluting gases:

W has the same meaning as V,

V represents:

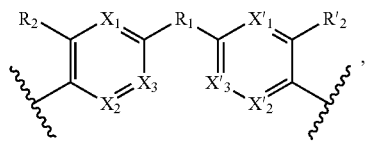

$X_1, X_2, X_3, X'_1, X'_2, X'_3, X_4, X_5, X_6, X_7, X'_4, X'_5, X'_6, X'_7$, $R_1, R_2, R'_2, R_3, R'_3, R_4$ and $R'_4$ are as defined above.

Said compounds can thus be represented by a general formula (I-2), which is more specific than (I):

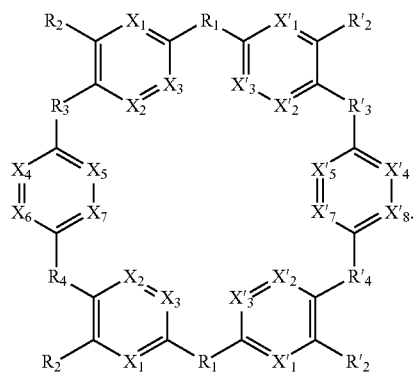
(I-2)

When:
$X_1=X_2=X_3=X'_1=X'_2=X'_3$,
$X_4=X_5=X_6=X_7=X'_4=X'_5=X'_6=X'_7$,
$R_2=R'_2$, and
$R_3=R'_3=R_4=R'_4$, then compounds of formula (I-2) are symmetrical compounds.

As an example of compound of general formula (I), and more particularly of formula (I-2), used for the detection, capture and/or separation of polluting gases, one can cited one of those selected from the group consisting of compounds of formula (I) wherein:

$R_1=SO_2$, $R_2=R'_2=NO_2$, $R_3=R'_3=R_4=R'_4=NH$ (19),
$R_1=SO_2$, $R_2=R'_2=NO_2$, $R_3=R=NH$, $R'_3=R'_4=S$ (20),
$R_1=S$, $R_2=R'_2=NO_2$, $R_3=R'_3=R_4=R'_4=NH$ (21),
$R_1=S$, $R_2=R'_2=NO_2$, $R_3=R_4=NH$, $R'_3=R'_4=S$ (22),
$R_1=SO_2$, $R_2=R'_2=NO_2$, $R_3=R'_3=S$, $R_4=R'_4=NH$ (23),
$R_1=S$, $R_2=R'_2=NO_2$, $R_3=R'_3=S$, $R_4=R'_4=NH$ (24),
and in each compound (19) to (24):
$X_1=X_2=X_3=X'_1=X'_2=X'_3=X_4=X_5=X_6=X_7=X'_4=X'_5=X'_6=X'_7=CH$.

Compounds (19) to (24) of formula (I-2) are represented in Table 2 below.

TABLE 2

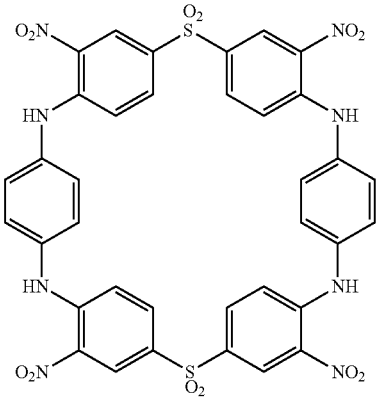
(19)

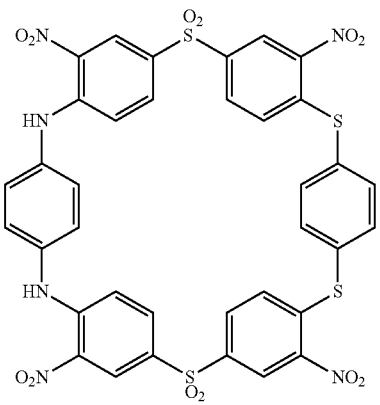 [SMILES: O=[N+]([O-])c1cc2ccc1Nc1ccc(cc1)Nc1ccc(cc1[N+](=O)[O-])S(=O)(=O)c1ccc(c([N+](=O)[O-])c1)Sc1ccc(cc1)Sc1ccc(cc1[N+](=O)[O-])S2(=O)=O]
(20)

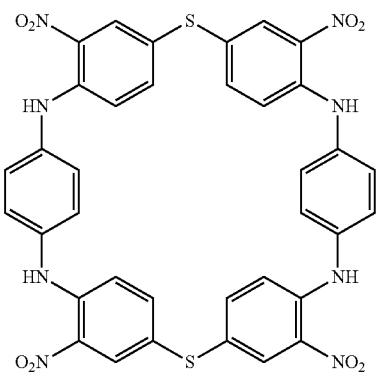 [SMILES: O=[N+]([O-])c1cc2ccc1Nc1ccc(cc1)Nc1ccc(cc1[N+](=O)[O-])Sc1ccc(c([N+](=O)[O-])c1)Nc1ccc(cc1)Nc1ccc(cc1[N+](=O)[O-])S2]
(21)

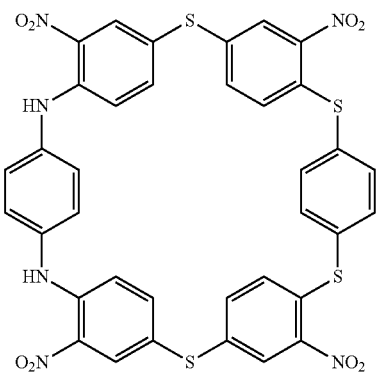 [SMILES: O=[N+]([O-])c1cc2ccc1Nc1ccc(cc1)Nc1ccc(cc1[N+](=O)[O-])Sc1ccc(c([N+](=O)[O-])c1)Sc1ccc(cc1)Sc1ccc(cc1[N+](=O)[O-])S2]
(22)

TABLE 2-continued

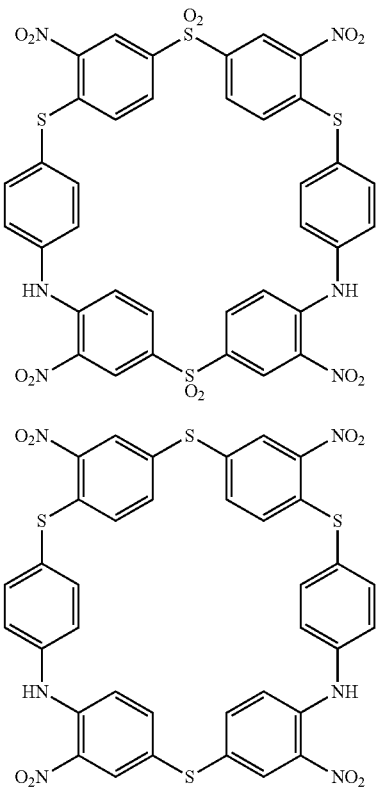

According to another embodiment of the invention, in compounds of formula (I) as defined above, used for the detection, capture and/or separation of polluting gases:

W, $R_4$ and $R'_4$ are absent,

V represents:

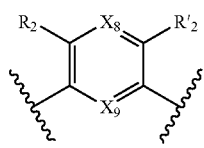

$X_4$, $X_5$, $X_6$, $X_7$, $X'_4$, $X'_5$, $X'_6$, $X'_7$, $X_8$, $X_9$ $R_2$, $R'_2$, $R_3$ and $R'_3$ are as defined above, and Y and Y' are as defined above when W is absent.

Said compounds can thus be represented by a general formula (I-3), which is more specific than (I):

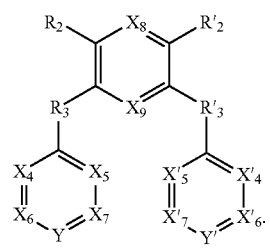

When:
$X_8=X_9$,
$X_4=X_5=X_6=X_7=X'_4=X'_5=X'_6=X'_7$,
$R_2=R'_2$,
$R_3=R'_3$ and,
$Y=Y'$, then compounds of formula (I-3) are symmetrical compounds.

As an example of compound of general formula (I), and more particularly of formula (I-3), used for the detection, capture and/or separation of polluting gases, one can cited one of those selected from the group consisting of compounds of formula (I) wherein:

Y=Y'=N, $R_2=R'_2=NO_2$ and $R_3=R'_3=S$ (25),
Y=Y'=CPO(OH)$_2$, $R_2=R'_2=NO_2$ and $R_3=R'_3=NH$ (26),
Y=Y'=CCH$_2$PO(OC$_2$H$_5$)$_2$, $R_2=R'_2=NO_2$, $R_3=R'_3=NH$ (27),
Y=Y'=CCOOH, $R_2=R'_2=NO_2$, $R_3=R'_3=S$ (28),
Y=Y'=CNH$_2$, $R_2=R'_2=CO_2Et$, $R_3=R'_3=S$ (29),
Y=Y'=CCOOH, $R_2=R'_2=CO_2Et$, $R_3=R'_3=S$ (30),
and in each compound (25) to (30):
$X_4=X_5=X_6=X_7=X'_4=X'_5=X'_6=X'_7=X_8=X_9=CH$.

Compounds (25) to (30) of formula (I-3) are represented in Table 3 below.

TABLE 3

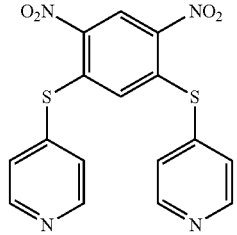 [SMILES: O=[N+]([O-])c1cc([N+](=O)[O-])c(Sc2ccncc2)cc1Sc1ccncc1]

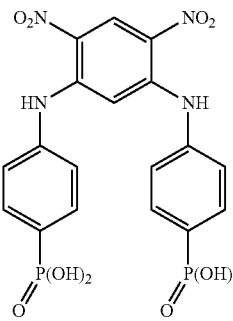

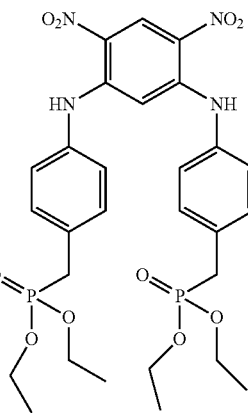

TABLE 3-continued

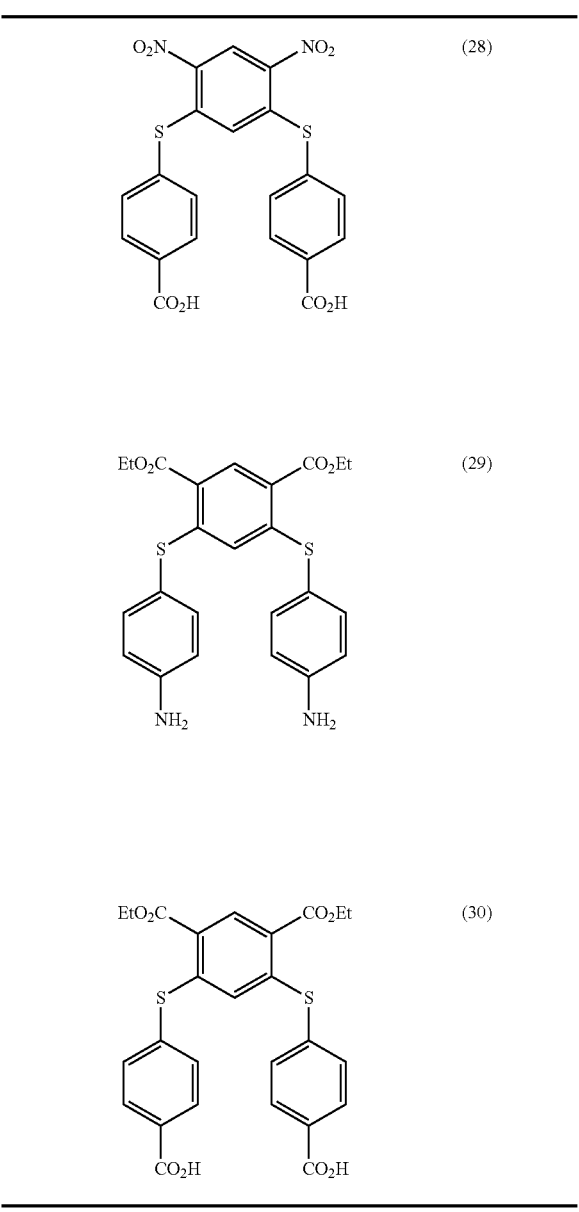

According to another embodiment of the invention, in compounds of formula (I) as defined above, used for the detection, capture and/or separation of polluting gases:

W has the same meaning as V,

V represents:

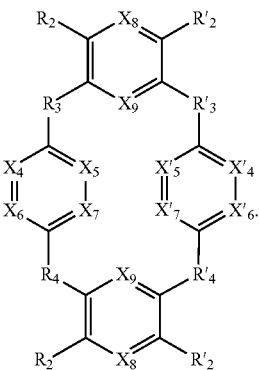

$X_4$, $X_5$, $X_6$, $X_7$, $X'_4$, $X'_5$, $X'_6$, $X'_7$, $X_8$, $X_9$, $R_2$, $R'_2$, $R_3$, $R'_3$, $R_4$ and $R'_4$ are as defined above.

Said compounds can thus be represented by a general formula (I-4), which is more specific than (I):

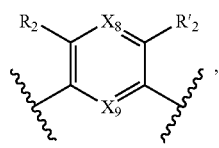
(I-4)

When:

$X_8 = X_9$, $X_4 = X_5 = X_6 = X_7 = X'_4 = X'_5 = X'_6 = X'_7$, $R_2 = R'_2$, $R_3 = R'_3 = R_4 = R'_4$, then compounds of formula (I-4) are symmetrical compounds.

As an example of compound of general formula (I), and more particularly of formula (I-4), used for the detection, capture and/or separation of polluting gases, one can cited one of those selected from the group consisting of compounds of formula (I) wherein:

$R_2 = R'_2 = NO_2$, $R_3 = R'_3 = R_4 = R'_4 = NH$ (31), $R_2 = R'_2 = NO_2$, $R_3 = R'_3 = R_4 = R'_4 = S$ (32), $R_2 = R'_2 = COOC_2H_5$, $R_3 = R'_3 = R_4 = R'_4 = S$ (33), $R_2 = R'_2 = NO_2$, $R_3 = R'_3 = S$, $R_4 = R'_4 = NH$ (34), and in each compound (31) to (34):

$X_4 = X_5 = X_6 = X_7 = X'_4 = X'_5 = X'_6 = X'_7 = X_8 = X_9 = CH$.

Compounds (31) to (34) of formula (I-4) are represented in Table 4 below.

TABLE 4

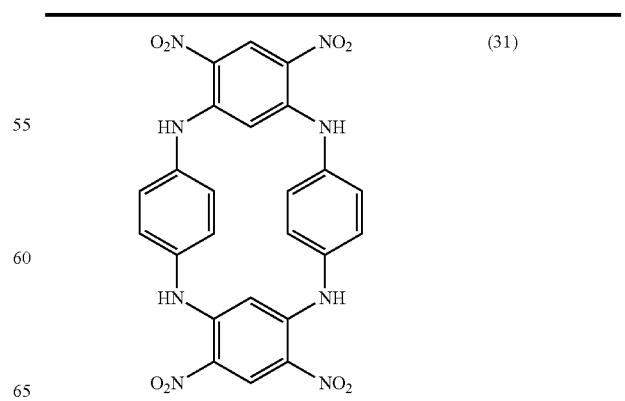

TABLE 4-continued

(32)
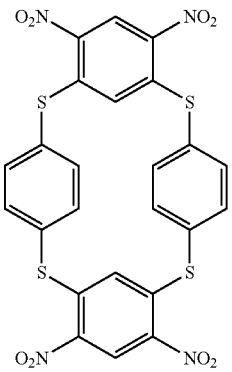 [SMILES: O=[N+]([O-])c1cc([N+](=O)[O-])c2cc1Sc1ccc(cc1)Sc1cc(c([N+](=O)[O-])cc1[N+](=O)[O-])Sc1ccc(cc1)S2]

(33)
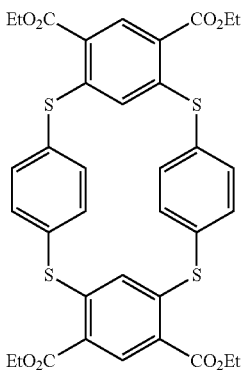 [SMILES: CCOC(=O)c1cc(C(=O)OCC)c2cc1Sc1ccc(cc1)Sc1cc(c(C(=O)OCC)cc1C(=O)OCC)Sc1ccc(cc1)S2]

(34)
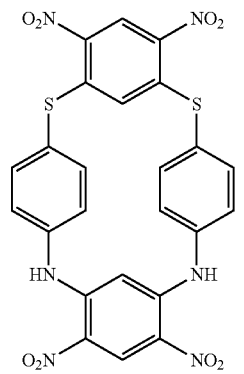 [SMILES: O=[N+]([O-])c1cc([N+](=O)[O-])c2cc1Nc1ccc(cc1)Sc1cc(c([N+](=O)[O-])cc1[N+](=O)[O-])Sc1ccc(cc1)N2]

According to one embodiment of the invention, compounds of formula (I), and more particularly of formula (I-1), (I-2), (I-3) and (I-4) are symmetrical compounds.

According to another embodiment of the invention, compounds of formula (I), and more particularly of formula (I-1), (I-2), (I-3) and (I-4) are not symmetrical compounds.

Compounds (I) of the invention, due to their structure, are particularly advantageous for their use for the detection, capture and/or separation of polluting gases. In fact, as mentioned above, compounds (I) are semi-rigid mesoporous and non-planar molecules having variable cavities bearing functional chemical groups which are able to interact specifically with gaseous or non-gaseous pollutants.

A subject of the invention is also a process for the depollution of the air and/or of toxic exhaust fumes, wherein the polluting agents present in said air and/or exhaust fumes are captured and/or separated into/by the compounds of general formula (I)) such as defined above, for their use for the detection, capture and/or separation of polluting gases.

The toxic exhaust fumes are for example those coming from the factories, the automobile or other transportation means, the indoor air pollution and also those found in biological fluids.

According to the invention, the polluting agents are gases selected from the group comprising carbon dioxide, methane, sulfur dioxide, nitrogen oxides, carbon monoxide, linear hydrocarbons, linear mono-olefins and their mixtures, and are preferably carbon dioxide.

Compounds

Another subject of the invention is a compound having the general formula (I):

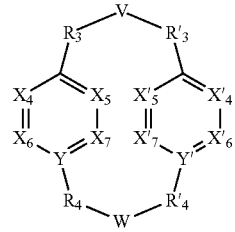
(I)

wherein
V represents:

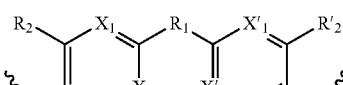 or

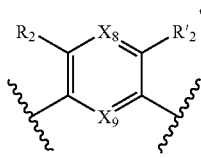

W has the same meaning as V or W is absent, and when W is absent then $R_4$ and $R'_4$ are also absent, $X_1, X_2, X_3, X'_1, X'_2, X'_3, X_4, X_5, X_6, X_7, X'_4, X'_5, X'_6, X'_7, X_8$ and $X_9$ are each independently N or a CH group, when W has the same meaning as V, then Y and Y' are each a carbon atom, when W is absent, then Y and Y' are each independently N or a CR group, with R representing H, $R_a$, $NR_aR_b$, $OR_a$, $SR_a$, $CO_2R_a$, $COR_a$, $CONHR_a$, $CONR_aR_b$, $NHCOR_a$, $SO_2R_a$, $SO_2NHR_a$, $SO_2NR_aR_b$, $PR_aR_b$, $P(O)R_aR_b$, $P(O)(OR_a)(OR_b)$, $CH_2PO(OR_a)(OR_b)$, $COCH_2COR_a$, $CSOR_a$, $CSR_a$, $CSNHR_a$, $CSNR_aR_b$, $NHCSR_a$, $P(S)R_aR_b$, $CSCH_2CSR_a$, $NHCONHR_a$, $NHCSNHR_a$ or a five or six-membered aromatic or heteroaromatic compound chosen from benzene, pyridine, diazine, triazine, tetrazine, pyrrole, thiophene, furan, azole, triazole or tetrazole, with $R_a$ and $R_b$ being each independently H, OH; an alkyl radical having from 1 to 10 carbon atoms (alkyl $C_1$-$C_{10}$); a five or six-membered carbocycle chosen from cyclohexane, piperidine, piperazine, tetrahydrothiophene, tetrahydropyrrole or dihydroazole; or an aromatic or heteroaromatic compound chosen from pyridine, diazine, triazine, tetrazine, pyrrole, thiophene, furan, azole, triazole, tetrazole, benzoazole, benzotriazole or indole, $R_1$ represents O, S, $SO_2$, SO, CO, a $NR_a$, $SiR_aR_b$, $SnR_aR_b$, $BR_a$ or a $PR_a$ group, $R_a$ and $R_b$ being as defined above, $R_2$ and $R'_2$ are each independently $COOR_a$, $NO_2$, $CONR_aR_b$, $SO_2R_a$, $SO_3H$, $OSO_3H$, $COR_a$, $PO_3H_2$, $OPO_3H_2$ or CN, $R_a$ and $R_b$ being as defined above, $R_3$, $R'_3$, $R_4$ and $R'_4$ are each independently S, $NR_a$, P, Se or Te, $R_a$ being as defined above, with the proviso that when W, $R_4$, $R'_4$ are absent, and V represents

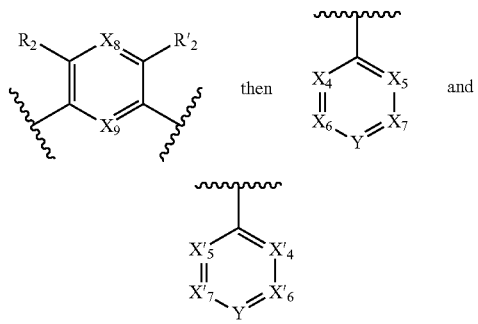

do not represent:

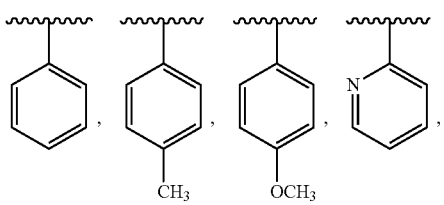

and with the proviso that the above formula (I) does not represent one of the seven following compounds wherein:

W is absent, V represents

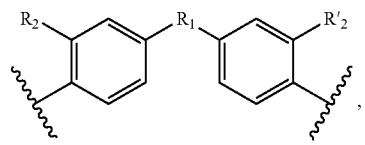

$X_4=X_5=X_6=X_7=X'_4=X'_5=X'_6=X'_7=CH$, and $Y=Y'=CNH_2$, $R_1=SO_2$, $R_2=R'_2=NO_2$, $R_3=R'_3=NH$;

W is absent, V represents

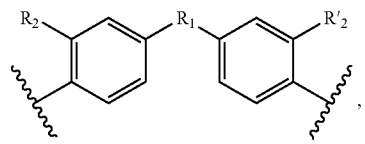

$X_4=X_5=X_6=X_7=X'_4=X'_5=X'_6=X'_7=CH$, and $Y=Y'=CNH_2$, $R_1=SO_2$, $R_2=R'_2=SO_3H$, $R_3=R'_3=S$ W is absent, V represents

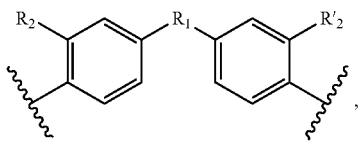

$X_4=X_5=X_6=X_7=X'_4=X'_5=X'_6=X'_7=CH$, and $Y=Y'=CNH_2$; $R_1=CO$; $R_2=R'_2=SO_3H$, $R_3=R'_3=S$;

W is absent, V represents

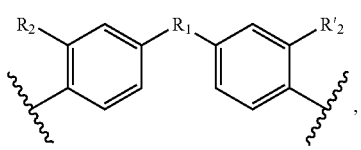

$X_4=X=X_6=X_7=X'_4=X'_5=X'_6=X'_7=CH$, and $Y=Y'=CH$, $R_1=SO_2$; $R_2=R'_2=NO_2$, $R_3=R'_3=S$;

$W=V=$

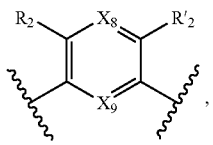

$X_4=X_5=X_6=X_7=X'_4=X'_5=X'_6=X'_7=CH$, and $Y=Y'=CH$, $R_3=R'_3=R_4=R'_4=S$, $R_2=R'_2=NO_2$, $X_8=X_9=CH$;

$W=V=$

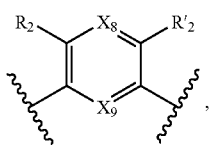

$X_4=X_5=X_6=X_7=X'_4=X=X_6=X=CH$, and $Y=Y'=CH$, $R_3=R'_3=R_4=R'_4=NH$, $R_2=R'_2=NO_2$, $X_8=X_9=CH$;

$W=V=$

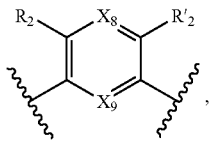

$X_4=X=X_6=X_7=X'_4=X'_5=X'_6=X'_7=CH$, and $Y=Y'=CH$, $R_3=R'_3=R_4=R'_4=NCH_3$, $R_2=R'_2=NO_2$, $X_8=X_9=CH$.

According to an embodiment of the invention, in the compounds of formula (I) as defined in the paragraph "compounds" above:

V represents:

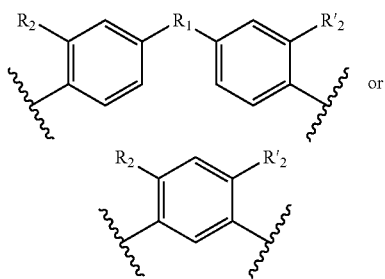

or $X_4$, $X_5$, $X_6$, $X_7$, $X'_4$, $X'_5$, $X'_6$ and $X'_7$ are each independently N or CH, when W has the same meaning as V, then Y and Y' are each a carbon atom, when W is absent, then Y and Y' are each independently N or a CR group, R being H, $NR_aR_b$, $CO_2R_a$, $P(O)(OR_a)(OR_b)$, $CH_2PO(OR_a)(OR_b)$, $R_1$ represents S, $SO_2$, $NR_a$ or O, $R_2$ and $R'_2$ are each independently $NO_2$, $COOR_a$, $COR_a$ or $CONR_aR_b$, $R_3$, $R'_3$, $R_4$ and $R'_4$ are each independently S or $NR_a$, with $R_a$ and $R_b$ are each independently H or an alkyl $C_1$-$C_{10}$.

In a particular embodiment of the invention, in compound of formula (I) as defined in the paragraph "compound" above, $X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $X_8$ and $X_9$ are each CH.

According to another embodiment of the invention, in the compounds of formula (I) as defined in the paragraph "compounds" above:

W, $R_4$ and $R'_4$ are absent,

V represents:

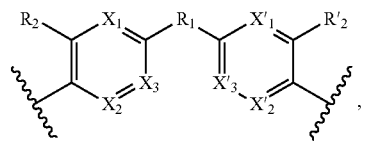

$X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $R_1$, $R_2$, $R'_2$, $R_3$ and $R'_3$ are as defined above, and Y and Y' are as defined above when W is absent.

Such compounds correspond to compounds of formula (I-1):

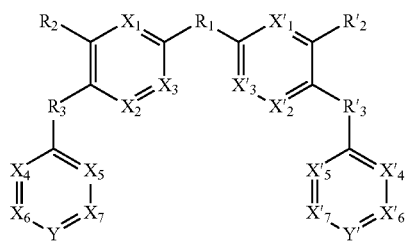

wherein $X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $R_1$, $R_2$, $R'_2$, $R_3$, $R'_3$, Y and Y' are as defined above.

As an example of compound of general formula (I), and more particularly of formula (I-1), one can cited one of those selected from the group consisting of compounds of formula (I) wherein:

Y=Y'=CNH$_2$, $R_1$=SO$_2$, $R_2$=R'$_2$=NO$_2$ and $R_3$=R'$_3$=S (1),

Y=Y'=CNH$_2$, $R_1$=SO$_2$, $R_2$=R'$_2$=NO$_2$ and $R_3$=R'$_3$=NH (2),

Y=Y'=N, $R_1$=SO$_2$, $R_2$=R'$_2$=NO$_2$ and $R_3$=R'$_3$=S (3),

Y=Y'=N, $R_1$=SO$_2$, $R_2$=R'$_2$=NO$_2$ and $R_3$=R'$_3$=NH (4),

Y=Y'=N, $R_1$=SO$_2$, $R_2$=R'$_2$=COOR$_a$ and $R_3$=R'$_3$=NH (5),

Y=Y'=N, R=SO$_2$, $R_2$=R'$_2$=COOR$_a$ and $R_3$=R'$_3$=S (6),

Y=Y'=N, $R_1$=S, $R_2$=R'$_2$=COOR$_a$ and $R_3$=R'$_3$=S (7),

Y=Y'=N, $R_1$=S, $R_2$=R'$_2$=COOR$_a$ and $R_3$=R'$_3$=NH (8),

Y=Y'=CNH$_2$, $R_1$=S, $R_2$=R'$_2$=COOR$_a$ and $R_3$=R'$_3$=NH (9),

Y=Y'=CNH$_2$, $R_1$=S, $R_2$=R'$_2$=COOR$_a$ and $R_3$=R'$_3$=S (10),

Y=Y'=CNH$_2$, $R_1$=S, $R_2$=R'$_2$=CONR$_a$R$_b$ and $R_3$=R'$_3$=S (11),

Y=Y'=CNH$_2$, $R_1$=S, $R_2$=R'$_2$=CONR$_a$R$_b$ and $R_3$=R'$_3$=NH (12),

Y=Y'=CNH$_2$, $R_1$=SO$_2$, $R_2$=R'$_2$=CONR$_a$R$_b$ and $R_3$=R'$_3$=NH (13), Y=Y'=CNH$_2$, $R_1$=SO$_2$, $R_2$=R'$_2$=CONR$_a$R$_b$ and $R_3$=R'$_3$=S (14), Y=Y'=N, $R_1$=SO$_2$, $R_2$=R'$_2$=CONR$_a$R$_b$ and $R_3$=R'$_3$=S (15), Y=Y'=N, $R_1$=SO$_2$, $R_2$=R'$_2$=CONR$_a$R$_b$ and $R_3$=R'$_3$=NH (16), Y=Y'=CCOOH, $R_1$=SO$_2$, $R_2$=R'$_2$=NO$_2$ and $R_3$=R'$_3$=S (17), Y=Y'=CCH$_2$PO(OC$_2$H$_5$)$_2$, $R_1$=SO$_2$, $R_2$=R'$_2$=NO$_2$ and $R_3$=R'$_3$=NH (18), and in each compound (1) to (18):

$X_1$=$X_2$=$X_3$=$X'_1$=$X'_2$=$X'_3$=$X_4$=$X_5$=$X_6$=$X_7$=$X'_4$=$X'_5$=$X'_6$=$X'_7$=CH, $R_a$ and $R_b$ are each independently H or an alkyl $C_1$-$C_{10}$.

Such compounds (1) to (18) are defined in Table 1 above.

According to another embodiment of the invention, in the compounds of formula (I) as defined in the paragraph "compounds" above:

W has the same meaning as V,

V represents:

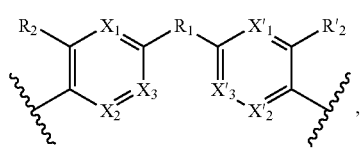

$X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $R_1$, $R_2$, $R'_2$, $R_3$, $R'_3$, $R_4$ and $R'_4$ are as defined above.

Such compounds correspond to compounds of formula (I-2):

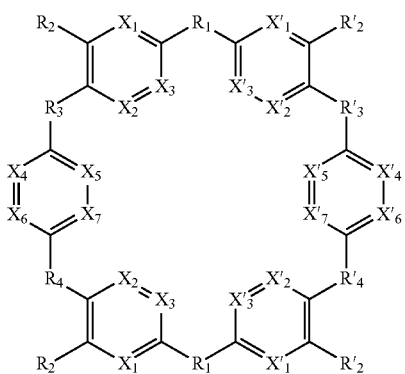

wherein $X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $R_1$, $R_2$, $R'_2$, $R_3$, $R'_3$, $R_4$, $R'_4$ are as defined previously.

As an example of compound of general formula (I), and more particularly of formula (I-2), one can cite one of those selected from the group consisting of compounds of formula (I) wherein:
$R_1$=$SO_2$, $R_2$=$R'_2$=$NO_2$, $R_3$=$R'_3$=$R_4$=$R'_4$=NH (19),
$R_1$=$SO_2$, $R_2$=$R'_2$=$NO_2$, $R_3$=$R_4$=NH, $R'_3$=$R'_4$=S (20),
$R_1$=S, $R_2$=$R'_2$=$NO_2$, $R_3$=$R'_3$=$R_4$=$R'_4$=NH (21),
$R_1$=S, $R_2$=$R'_2$=$NO_2$, $R_3$=$R_4$=NH, $R'_3$=$R'_4$=S (22),
$R_1$=$SO_2$, $R_2$=$R'_2$=$NO_2$, $R_3$=$R'_3$=S, $R_4$=$R'_4$=NH (23),
$R_1$=S, $R_2$=$R'_2$=$NO_2$, $R_3$=$R'_3$=S, $R_4$=$R'_4$=NH (24),
and in each compound (19) to (24):
$X_1$=$X_2$=$X_3$=$X'_1$=$X'_2$=$X'_3$=$X_4$=$X_5$=$X_6$=$X_7$=$X'_4$=$X'_5$=$X'_6$=$X'_7$=CH.

Such compounds (19) to (24) are defined in Table 2 above

According to another embodiment of the invention, in the compounds of formula (I) as defined in the paragraph "compounds" above:
W, $R_4$ and $R'_4$ are absent,
V represents:

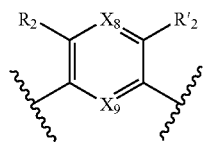

$X_4$, $X_5$, $X_6$, $X_7$, $X'_4$, $X'_5$, $X'_6$, $X'_7$, $X_8$, $X_9$ $R_2$, $R'_2$, $R_3$ and $R'_3$ are as defined above, and Y and Y' are as defined above when W is absent.

Such compounds correspond to compounds of formula (I-3):

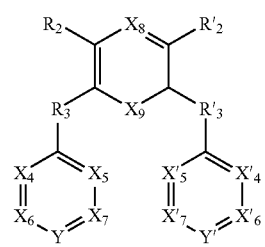

wherein $X_4$, $X_5$, $X_6$, $X_7$, $X'_4$, $X'_5$, $X'_6$, $X'_7$, $X_8$, $X_9$, $R_2$, $R'_2$, $R_3$, $R'_3$, Y and Y' are as defined previously.

As an example of compound of general formula (I), and more particularly of formula (I-3), one can cite one of those selected from the group consisting of compounds of formula (I) wherein:
Y=Y'=N, $R_2$=$R'_2$=$NO_2$ and $R_3$=$R'_3$=S (25),
Y=Y'=CPO(OH)$_2$, $R_2$=$R'_2$=$NO_2$ and $R_3$=$R'_3$=NH (26),
Y=Y'=CCH$_2$PO(OC$_2$H$_5$)$_2$, $R_2$=$R'_2$=$NO_2$, $R_3$=$R'_3$=NH (27),
Y=Y'=CCOOH, $R_2$=$R'_2$=$NO_2$, $R_3$=$R'_3$=S (28),
Y=Y'=CNH$_2$, $R_2$=$R'_2$=CO$_2$Et, $R_3$=$R'_3$=S (29),
Y=Y'=CCOOH, $R_2$=$R'_2$=CO$_2$Et, $R_3$=$R'_3$=S (30),
and in each compound (25) to (30):
$X_4$=$X_5$=$X_6$=$X_7$=$X'_4$=$X'_5$=$X'_6$=X=$X_8$=$X_9$=CH.

Such compounds (25) to (30) are defined in Table 3 above

According to another embodiment of the invention, in compounds of formula (I) as defined in the paragraph "compounds" above:
W has the same meaning as V,
V represents:

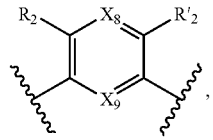

$X_4$, $X_5$, $X_6$, $X_7$, $X'_4$, $X'_5$, $X'_6$, $X'_7$, $X_8$, $X_9$, $R_2$, $R'_2$, $R_3$, $R'_3$, $R_4$ and $R'_4$ are as defined above.

Such compounds correspond to compounds of formula (I-4):

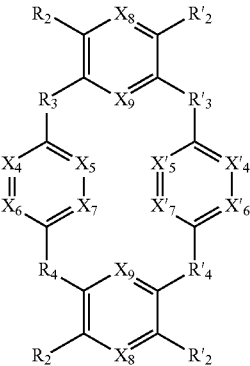

wherein $X_4$, $X_5$, $X_6$, $X_7$, $X'_4$, $X'_5$, $X'_6$, $X'_7$, $X_8$, $X_9$, $R_2$, $R'_2$, $R_3$, $R'_3$, $R_4$, $R'_4$ are as defined previously.

As an example of compound of general formula (I), and more particularly of formula (I-4), one can cite one of those selected from the group consisting of compounds of formula (I) wherein:
$R_2$=$R'_2$=CO$_2$Et, $R_3$=$R'_3$=$R_4$=$R'_4$=S (33),
$R_2$=$R'_2$=$NO_2$, $R_3$=$R'_3$=S, $R_4$=$R'_4$=NH (34),
and in each compound (33) to (34):
$X_4$=$X_5$=$X_6$=$X_7$=$X'_4$=$X'_5$=$X'_6$=X=$X_8$=$X_9$=CH.

Compounds (33) and (34) are listed in Table 4 above.

Process

Another subject of the invention is also a process for the preparation of compounds of formula (I), such a process being for example such as defined in the following reaction scheme (one-pot or iterative synthesis):

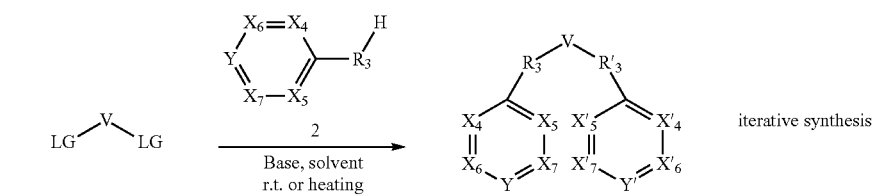
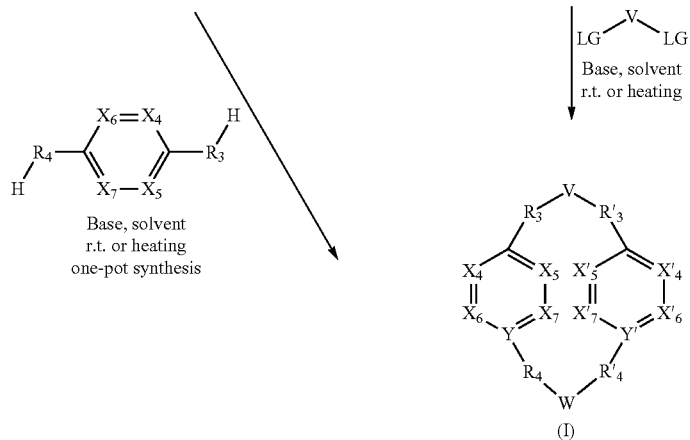
The process for the preparation of compounds of formula (I-1) can for example be defined by the following reaction scheme:
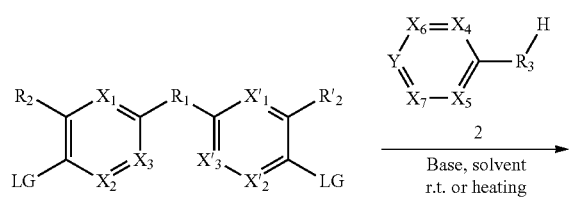
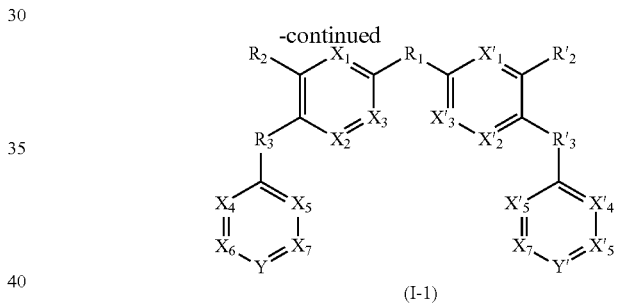
LG is a leaving group, preferably selected from halogen, tosylate, mesylate or ammonium.
The process for the preparation of compounds of formula (I-2) can for example be defined by the following reaction scheme (via iterative pathway):
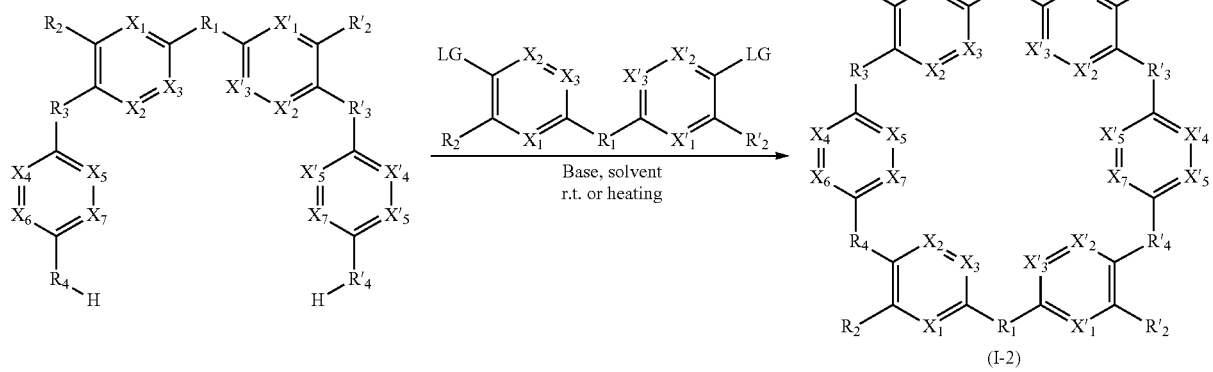

The process for the preparation of compounds of formula (I-3) can for example be defined by the following reaction scheme:

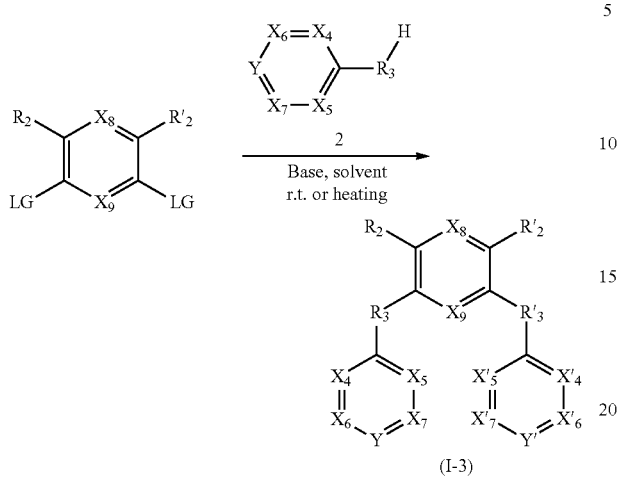

The process for the preparation of compounds of formula (I-4) can for example be defined by the following reaction scheme:

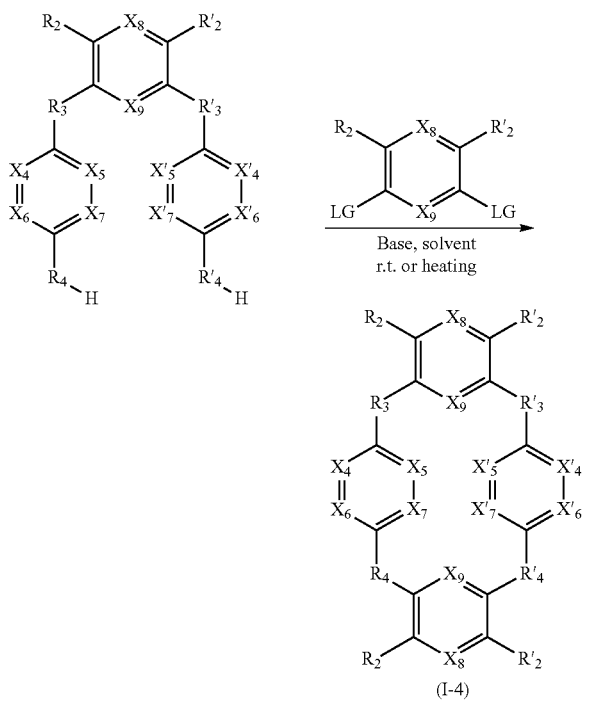

Further aspects and advantages of this invention will be disclosed in the following figures and examples, which should be regarded as illustrative and not limiting the scope of this application.

EXAMPLES

Figure 1:
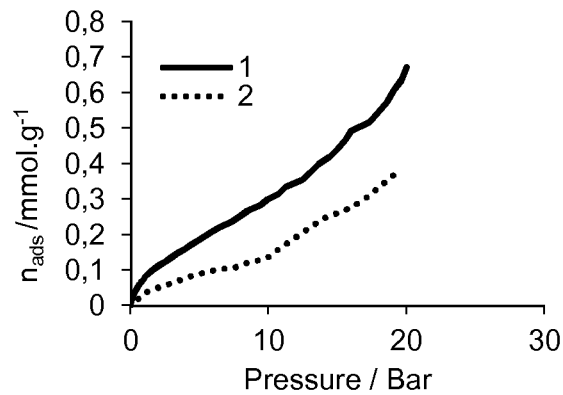
FIG. 1: adsorption isotherms of compounds (1) and (2) of general formula (I), and more particularly of formula (I-1), for carbon dioxide at 303° K.

Example 1: General Synthesis Protocol of Compounds of General Formula (I)

1. General Synthesis Protocol of Compounds of General Formulae (I-1) and (I-3)

To a solution of a di-halogenated (or an analogous) derivative (1 equiv.) in a polar solvent (or a mixture of polar solvents) was added a thiol or amino derivative (2.6 equiv.) and a base (such as DIPEA (diisopropylethylamine, Hünig base), NaH, $Cs_2CO_3$, $K_2CO_3$, NaOH etc. (2.6 equiv.)) or was added to the reaction mixture. The reaction was heated to reflux or stirred at room temperature and then cooled down to room temperature. The obtain precipitate was filtered off and washed successively with ethanol and water. The obtained solid was dried under vacuum affording the cyclic compound as a colored solid.

1.1. Synthesis of Compound (1) of the Invention (Formula (I-1)):

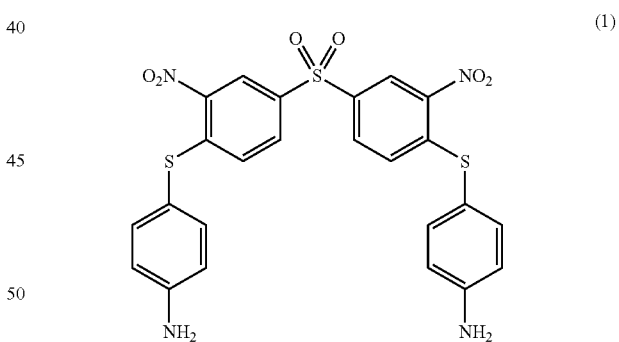

To a solution of 0.80 g (2.30 mmol) of bis-(4-fluoro-3-nitrophenyl) sulfone in 50 mL of a mixture of ethanol/$CH_3CN$ (v:v) was added, at room temperature, 0.760 g (6.00 mmol) of 4-aminothiophenol. To this reaction mixture was added 0.980 mL of DIPEA. Within 2 min an orange precipitate appeared. The reaction was heated to reflux during 3 h then cooled down to room temperature and then filtered off. The obtained solid was washed with ethanol (50 mL), then with hot water (50 mL) and finally with 50 mL of ethanol. After drying under reduced pressure, a yellow solid (1) was obtained in 92% yield. The melting point is 314.20° C. $^1$H NMR (250 MHz, DMSO $d_6$) δ 8.63 (d, J=1.9 Hz, 2H), 8.06 (dd, J=8.7, 1.9 Hz, 2H), 7.18 (d, J=8.4 Hz, 4H), 6.99 (d, J=8.7 Hz, 2H), 6.68 (d, J=8.4 Hz, 4H), 5.82 (s, 4H). $^{13}$C NMR (62.50 MHz, DMSO d$_6$) δ 151.46, 148.33, 143.51, 137.00, 136.15, 131.61, 128.95, 125.17, 115.26, 110.60. ESI-MS: 555.1 m/z [M+H]$^+$. 577.1 m/z [M+Na]$^+$. EA calculated for C$_{24}$H$_{18}$N$_4$O$_6$S$_3$: N, 10.10; C, 51.97; H, 3.27; S, 17.34; found: N, 9.89; C, 51.77; H, 3.21; S, 17.98.

1.2. Synthesis of Compound (2) of the Invention (Formula (I-1):

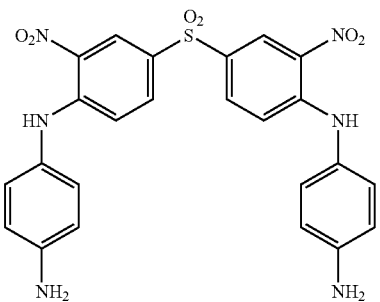

(2)

To a solution of 0.69 g (1 mmol) of bis-(4-fluoro-3-nitrophenyl) sulfone in 50 mL of a mixture of ethanol/CH$_3$CN (20:30) was added simultaneously at 0° C., 1.66 mL (10.00 mmol) of DIPEA and 1.08 g (6.00 mmol) of 1,4-diaminobenzene dihydrochloride. The reaction mixture was warmed up and heated under reflux over 18 hours. During the course of the reaction a dark brown precipitate was formed. The reaction mixture was cooled down to room temperature and then filtered off. The obtained brown precipitate was washed with ethanol (50 mL), then with hot water (50 mL) and finally with 50 mL of ethanol again. The brown solid was dried under reduced pressure, and a brown solid (2) is obtained in 71% yield. The melting point is 285.28° C. $^1$H NMR (250 MHz, DMSO d$_6$) δ 9.74 (s, 2H), 8.51 (d, J=2.3 Hz, 2H), 7.79 (dd, J=9.2, 2.2 Hz, 2H), 6.93 (dd, J=8.9, 2.8 Hz, 6H), 6.61 (d, J=8.6 Hz, 4H), 5.27 (s, 4H). $^{13}$C NMR (62.50 MHz, DMSO d$_6$) δ 147.57, 146.70, 132.58, 130.05, 126.76, 126.13, 124.81, 117.19, 113.95. ESI-MS: 521.1 m/z [M+H]$^+$. 543.1 m/z [M+Na]$^+$. EA calculated for C$_{24}$H$_{20}$N$_6$O$_6$S: N, 16.15; C, 55.38; H, 3.87; S, 6.16; found: N, 15.70; C, 54.56; H, 3.76; S, 6.23.

1.3. Synthesis of Compound (25) of the Invention (Formula (I-3):

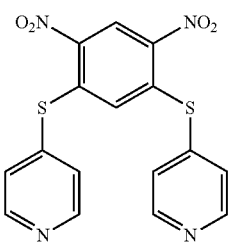

(25)

To a solution of 1.500 g of 4-mercaptopyridine (13.5 mmol) in 20 mL of dry THF was slowly added, at 0° C. under an argon atmosphere, 0.346 g of NaH (14.40 mmol, 60% in mineral oil). The reaction mixture was kept 1 hour under stirring then 1.25 g of 1,5-difluoro-2,4-dinitrobenzene (6.14 mmol) in 10 mL of dry THF was added dropwise. The reaction mixture was stirred at room temperature over 18 h. To the dark brown solution was added 50 mL of water and the precipitate obtained was filtered off and washed with ethanol (70 ml). The pale yellow solid was dried affording compound 25 in 68% yield. $^1$H NMR (250 MHz, DMSO) δ 9.02 (s, 1H), 8.52 (dd, J=4.6, 1.3 Hz, 4H), 7.39 (dd, J=4.5, 1.4 Hz, 4H), 6.42 (s, 1H). $^{13}$C NMR (101 MHz, DMSO d6) δ 151.02, 141.88, 141.09, 138.16, 128.28, 126.63, 123.68. ESI-MS: 387 m/z [M+H]$^+$. 393 m/z [M+Li]$^+$. EA calculated for C$_{16}$H$_{10}$N$_4$O$_4$S$_2$: N, 14.50; C, 49.73; H, 2.61; S, 16.60 found: N, 14.78; C, 49.06; H, 2.49; S, 16.46.

2. General Synthesis Protocol of Compounds of General Formulae (I-2) and (I-4) (Cyclic Compounds)

Iterative Synthesis:

To a solution of compound (formula I-1 or I-3) in a polar solvent was added a di-halogenated (or an analogous) derivative (1 equiv) followed by a base (2.5 equiv). The reaction mixture was stirred at room temperature or under reflux. Solvent was added or not to precipitate the cyclic derivative. The precipitate was filtered off and washed successively with water and a polar solvent such as ethanol. The solid was finally dried under reduce pressure to afford the pure compound.

One-Pot Synthesis:

To a solution of a di-halogenated (or an analogous) derivative (1 equiv.) in a polar solvent (or a mixture of polar solvents) was added an aromatic compound bearing two acidic groups (such as SH, NH$_2$, OH etc. (1 equiv.) followed by a base (2.5 equiv.). The reaction was heated to reflux or stirred at room temperature and then cooled down to room temperature. The obtain precipitate was filtered off and washed successively with ethanol and water. The obtained solid was dried under vacuum affording the corresponding compound as a solid.

2.1. Synthesis of Compound (19) of the Invention (Formula (I-2):

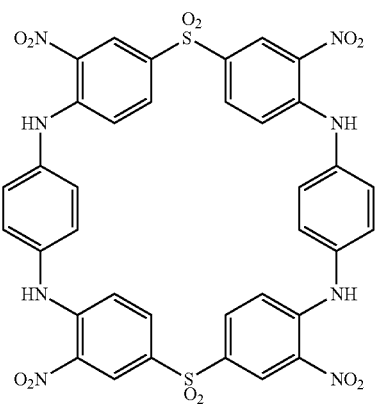

(19)

To a solution of 0.91 mmol of compound 2 in 30 mL of dimethylformamide (DMF) was added, at room temperature, a solution of 1.05 mmol of bis-(4-fluoro-3-nitrophenyl) sulfone) in 5 mL of DMF and 2.91 mmol of diisopropylethylamine (DIPEA). The reaction mixture was heated (90° C.) under magnetic stirring over 5 days. After that, 50 mL of acetonitrile (CH$_3$CN) were added to precipitate the product and the material was filtered. The obtained solid was carefully washed with 100 mL of CH$_3$CN. The dark red solid was dried under reduced pressure affording the macrocycle in 51%. $^1$H NMR (250 MHz, DMSO$_{d6}$) δ (ppm): 9.91 (s, 4H); 8.58 (s, 4H); 7.91 (d, J=7.90 Hz, 4H); 7.41 (s, 8H); 7.19 (d, J=8.80 Hz, 4H). ESI-MS (m/z): 823 [M−H]$^+$. EA calculated for $C_{38}H_{24}N_8O_{12}S_2$: C: 52.43; H: 2.93; N: 13.59; S: 7.77; found: C: 52.53; H: 2.92; N: 12.84; S: 7.52.

2.2. Synthesis of Compound (31) of the Invention (Formula (I-4):

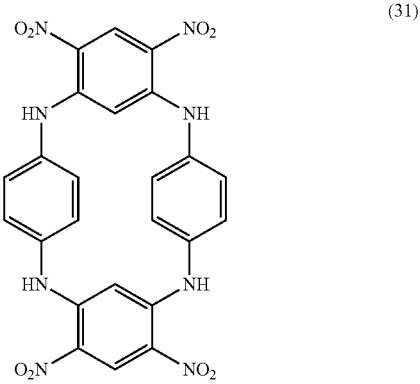 [SMILES: O=[N+]([O-])c1cc([N+](=O)[O-])c2cc1[nH]c1ccc(cc1)[nH]c1cc([nH]c3ccc(cc3)[nH]2)c([N+](=O)[O-])cc1[N+](=O)[O-]]

(31)

To a solution of N, N'-(4,6-dinitro-1,3-phenylene)dibenzene-1,4-diamine in $CH_3CN$ in the presence of DIPEA (5 equiv) was added 1,5-difluoro-2,4-dinitrobenzene (1 equiv.). The reaction mixture was refluxed under reflux to afford a precipitate of 31, which was isolated by filtration in 84% yield. 31 could not be characterized in solution by $^1H$ NMR due its lack of solubility even in DMSO. MS (ESI): 543 [M−H]+; EA calculated for $C_{24}H_{16}N_8O_8$: C, 52.95; H, 2.96; N, 20.58; found: C, 52.44; H, 3.07; N, 20.22.

Example 2: Gas Adsorption Measurements of Compounds of General Formula (I)

Method:

Compounds of general formula (I), and more particularly of formula (I-1), (I-2), (I-3) and (I-4) were tested for gas adsorption measurements, for instance $CO_2$ and $CH_4$, and results are reported on FIGS. 1 to 6.

0.40 g of sample was used. Prior to each experiment, samples were outgassed ex situ at 333° K for 16 h under a secondary vacuum of $10^{-3}$ mbar. High-pressure gas adsorption measurements were carried out at 303 K (Kelvin) and up to 30 bars with $CO_2$ and $CH_4$ using a homemade high-throughput instrument[5]. However, most differences in the data are visible up to 2 bars. The gases were obtained from Air Liquide. Methane ($CH_4$) was of 99.9995% purity, carbon dioxide ($CO_2$) was of 99.995% purity.

Gas adsorption is measured via a manometric gas dosing system on six samples in parallel with a point-by-point introduction of gas to the sample. The amounts of gas adsorbed are calculated by an equation of state using the Reference Fluid Thermodynamic and Transport Properties (REFPROP) software package 8.0 of the National Institute of Standards and Technology (NIST)[6]. This experimental device is convenient because only 100 mg of sample is used, and each sample can be thermally activated individually in situ under primary vacuum, at a given final temperature overnight (here around 50-60° C.).

Adsorption experiments were combined with microcalorimetry. The adsorption enthalpy was obtained by coupling that kind of system with a Tian-Calvet type microcalorimeter.

In this case, the experimental device allows the determination of the adsorption isotherm and the adsorption enthalpy simultaneously. An exothermic thermal effect accompanied each introduction. This peak in the curve of energy with time has to be integrated to provide an integral (or pseudo-differential) molar enthalpy of adsorption for each dose.

1. Gas Adsorption Measurements of Compounds (1) and (2) (Formula (I-1))

Figure 2:
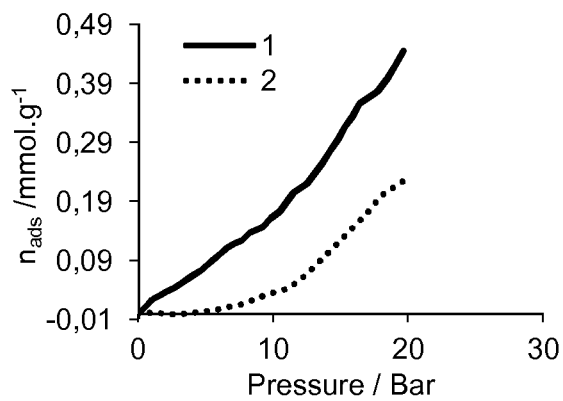
FIG. 2: adsorption isotherms of compounds (1) and (2) of general formula (I), and more particularly of formula (I-1), for methane at 303° K.

FIGS. 1 and 2 show respectively the adsorption isotherms of compounds (1) and (2) for carbon dioxide ($CO_2$) (FIG. 1) and methane ($CH_4$) (FIG. 2).

These measurements are relevant up to 20 bars approximately. Indeed, above 20 bars we observe a slight increase the amount adsorbed whereas we expect more something like a plateau, according to the global shape of the adsorption isotherm, indicating a kind of saturation of the sample. This behavior is more an artifact of the experimental device, which is more pronounced when the adsorption is weak.

The difference between compounds (1) and (2) provides from the replacement of two sulfurs present in compound (1) by two secondary amine functions in compound (2).

Compound (1) is most efficient for molecule adsorption than compound (2). It could be deduced than sulfur functions accompanied by primary amine function on phenyl groups are more efficient for molecule adsorption than other combinations.

Figure 3:
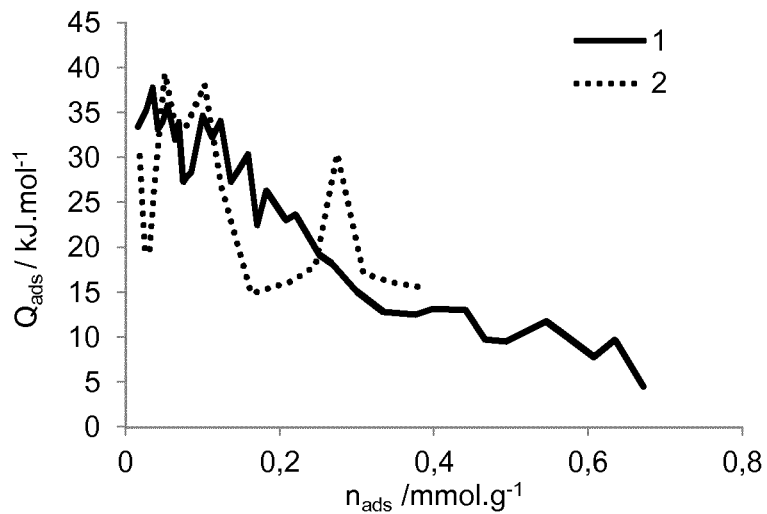
FIG. 3: differential enthalpies of adsorption of carbon dioxide for compounds (1) and (2) of general formula (I), and more particularly of formula (I-1), at 303° K.

The differential enthalpies of adsorption of carbon dioxide for compounds (1) and (2) are reported on FIG. 3. The enthalpy of adsorption for the samples in the low-pressure region is in the range −30 to −35 $kJ \cdot mol^{-1}$. The enthalpies of adsorption decrease with increasing loading to reach a value at approximately −10 $kJ \cdot mol^{-1}$.

This value is not representative of a real adsorption behavior because if adsorption is still occurring in a system the resulting enthalpies must be higher or at least equal to the enthalpy of liquefaction of $CO_2$ (−17.5 $kJ \cdot mol^{-1}$). When the energetic values measured/calculated drop below the enthalpy of liquefaction of $CO_2$ it means that the adsorption phenomenon is very poor and these values are a combination of various effects/errors, and couldn't help to the understanding of the system in this domain. These trends (the decreasing energetic profile) suggest that at low pressure, adsorption occurs on specific sites prior to coverage of the remaining surface. According to the literature[7], this value of −35 kJ $mol^{-1}$ is in the same order of magnitude than that could be attempt for carbon dioxide adsorption with some metal-organic frameworks materials.

Regenerability of the sample has been evaluated under mild conditions. Indeed for each gas ($CO_2$ and $CH_4$) two measurements with the same parameters are performed on the sample. Between the first experiment and the second experiment, the sample is submitted to an evacuation step at 30° C. and under primary vacuum during one hour. By this way, from the second gas adsorption measurement the regenerability/recovery of the sample can be checked under these conditions.

2. Gas Adsorption Measurements of Compounds (25) and (28) (Formula (I-3))

Figure 6:
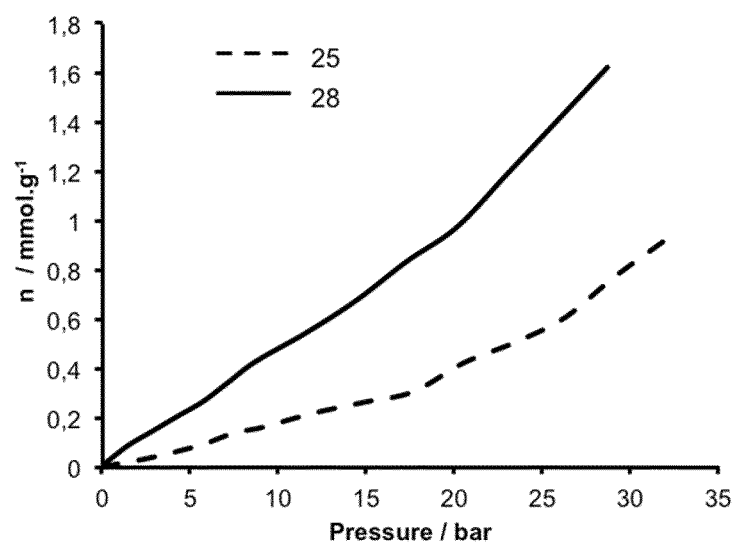
FIG. 6: adsorption isotherms of compounds (25) and (28) of general formula (I), and more particularly of formula (I-3), for carbon dioxide at 303° K.

From FIG. 6 one can deduce that the chemical groups at the periphery affect dramatically the adsorption properties of the acyclic compounds regardless the cavity size. The chemical groups at the periphery will affect both the supramolecular intermolecular interactions and the interaction with the pollutant. Compound (28) is more efficient for $CO_2$ adsorption than compound (25). The only difference between the two open-chain structures is related to their end-substitution. The latter will modify the porosity of the bulk material through the formation of a possible 3D-supramolecular network, which will affect the adsorption properties in conjunction with its direct interaction with the pollutant.

3. Gas Adsorption Measurements of Compounds (2) (Formula (I-1)), (19) (Formula (I-2) and (31) (Formula (I-4))

Figure 4:
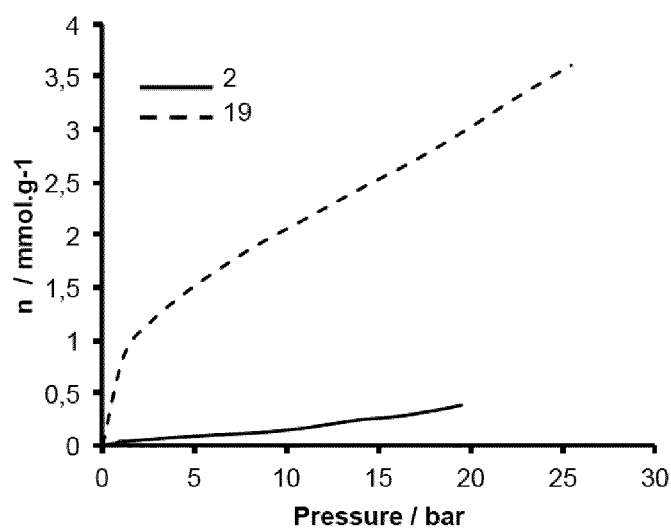
FIG. 4: adsorption isotherms of compounds (2) (formula (I-1)) and (19) (formula (I-2)) of general formula (I), for carbon dioxide at 303° K.
Figure 5:
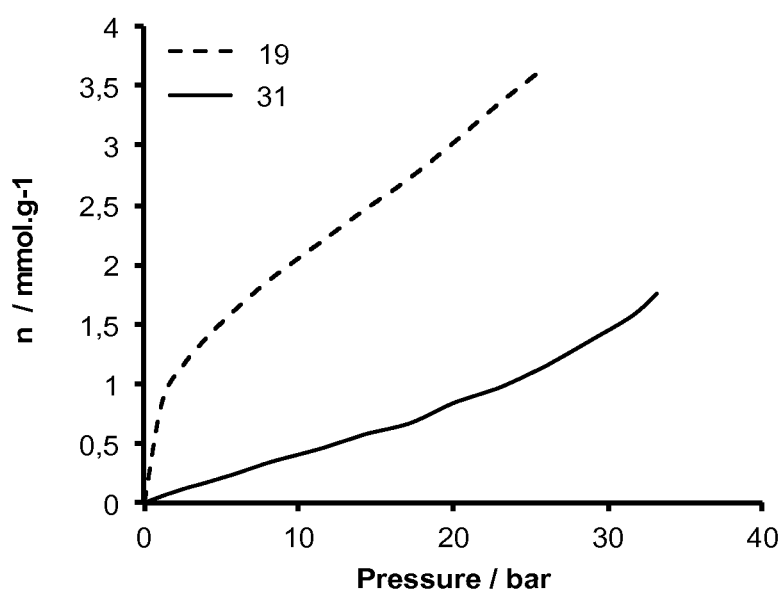
FIG. 5: adsorption isotherms of compounds (19) (formula (I-2)) and (31) (formula (I-4)) of general formula (I), for carbon dioxide at 303° K.

One can deduce from FIG. 4 that compound (19) (cyclic compound) is most efficient for molecule adsorption than compound (2), which represents the open-chain analogue of compound (19). Thus the effect of the macrocyclic structure (compound 19) is to increase the ligand field strength. One can also deduce from FIG. 5 that compound (19) (cyclic compound) is most efficient for molecule adsorption than compound (31). Thus the larger cavity present in compound (19) (compared to the cavity present in compound (31)) led to greater amount of $CO_2$ adsorbed.

Conclusion on the Adsorption Properties of Compounds of Formula (I)

Compounds of formula (I) have demonstrated efficient adsorption properties toward gaseous pollutant such as $CO_2$ and $CH_4$ for instance. Owing their non-planar structures, compounds of formula (I) lead to porous bulk material in which the adsorption efficiency can be governed and modulated by several structural factors. Generally speaking open-chain compounds of formula I-1 and I-3 exhibit a lower efficiency compared to their cyclic counterparts of formula I-2 and I-4. The peripheral substituents dramatically affect the adsorption properties by varying the bulk material porosity and governing the interactions with the pollutants. In addition, the cavity sizes of the compounds of formula (I) modulate the adsorption efficiency. Thus, compounds having larger cavities in conjunction with the appropriate substituents present the highest adsorption capabilities. Cyclic structures of formula I-2 exhibit higher adsorption efficiencies compared to the cyclic structures of formula I-3 due to larger cavities.

BIBLIOGRAPHY

1. N. Stem, Stem Review on the Economics of Climatic Change, Cambridge University Press, Cambridge, 2006.
2. B. Metz et al., Intergovernmental Panel on Climate Change, Special Report on Carbon Dioxide Capture and Storage, Cambridge University press, Cambridge, 2005, http://www.ipcc.ch/.
3. M. Z. Jacobson, Energy Environ. Sci. 2009, 2,148.
4. D. M. D'Alessandro et al., Carbon Dioxide Capture, Angew. Chem. Int. Ed., 2010, 49, pp. 6058-6082.
5. Wiersum, A. D.; Giovannangeli, C.; Vincent, D.; Bloch, E.; Reinsch, H.; Stock, N.; Lee, J. S.; Chang, J.-S.; Llewellyn, P. L. ACS Comb. Sci. 2013, 15, 111-119.
6. Lemmon, E. W.; McLinden, H. M. *MO Reference Fluid Thermodynamic and Transport Properties*; REFPROP 8.0; National Institute of Standards and Technology: Gaithersburg, Md., 2007.
7. X.-J. Hou, P. He, H. Li and X. Wang, *J. Phys. Chem. C*, 2013, 117, 2824-2834.

The invention claimed is:

1. A method for the detection, capture and/or separation of polluting gases, comprising capture and/or separation into/by a compound having general formula (I)

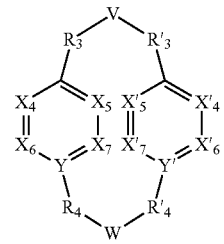

(I)

wherein

V represents:

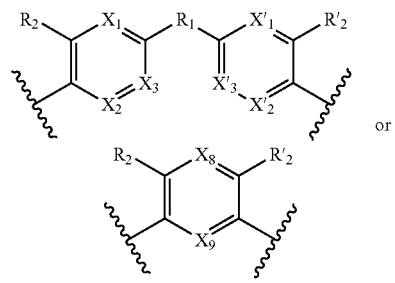

or

W has the same meaning as V or W is absent, and when W is absent then $R_4$ and $R'_4$ are also absent, $X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $X_8$ and $X_9$ are each independently N or a CH group, when W has the same meaning as V, then Y and Y' are each a carbon atom, when W is absent, then Y and Y' are each independently N or a CR group, with R representing H, $R_a$, $NR_aR_b$, $OR_a$, $SR_a$, $CO_2R_a$, $COR_a$, $CONHR_a$, $CONR_aR_b$, $NHCOR_a$, $SO_2R_a$, $SO_2NHR_a$, $SO_2NR_aR_b$, $PR_aR_b$, $P(O)R_aR_b$, $P(O)(OR_a)(OR_b)$, $CH_2PO(OR_a)(OR_b)$, $COCH_2COR_a$, $CSOR_a$, $CSR_a$, $CSNHR_a$, $CSNR_aR_b$, $NHCSR_a$, $P(S)R_aR_b$, $CSCH_2CSR_a$, $NHCONHR_a$, $NHCSNHR_a$ or a five or six-membered aromatic or heteroaromatic compound chosen from benzene, pyridine, diazine, triazine, tetrazine, pyrrole, thiophene, furan, azole, triazole or tetrazole, with $R_a$ and $R_b$ being each independently H, OH; an alkyl radical having from 1 to 10 carbon atoms (alkyl $C_1$-$C_{10}$); a five or six-membered carbocycle chosen from cyclohexane, piperidine, piperazine, tetrahydrothiophene, tetrahydropyrrole or dihydroazole; or an aromatic or heteroaromatic compound chosen from pyridine, diazine, triazine, tetrazine, pyrrole, thiophene, furan, azole, triazole, tetrazole, benzoazole, benzotriazole or indole, $R_1$ represents O, S, $SO_2$, SO, CO, a $NR_a$, $SiR_aR_b$, $SnR_aR_b$, $BR_a$ or a $PR_a$ group, $R_a$ and $R_b$ being as defined above, $R_2$ and $R'_2$ are each independently $COOR_a$, $NO_2$, $CONR_aR_b$, $SO_2R_a$, $SO_3H$, $OSO_3H$, $COR_a$, $PO_3H_2$, $OPO_3H_2$ or CN, $R_a$ and $R_b$ being as defined above, $R_3$, $R'_3$, $R_4$ and $R'_4$ are each independently S, $NR_a$, P, Se or Te, $R_a$ being as defined above.

2. A method according to claim 1, wherein in the compound of formula (I):

V represents:

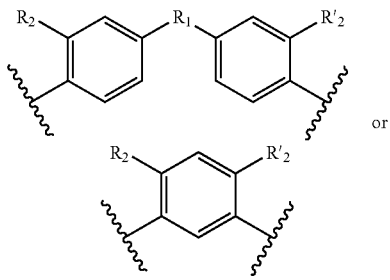 or $X_4$, $X_5$, $X_6$, $X_7$, $X'_4$, $X'_5$, $X'_6$ and $X'_7$ are each independently N or CH, when W has the same meaning as V, then Y and Y' are each a carbon atom, when W is absent, then Y and Y' are each independently N or a CR group, R being H, $NR_aR_b$, $CO_2R_a$, $P(O)(OR_a)(OR_b)$, $CH_2PO(OR_a)(OR_b)$, $R_1$ represents S, $SO_2$, $NR_a$ or O, $R_2$ and $R'_2$ are each independently $NO_2$, $COOR_a$, $COR_a$ or $CONR_aR_b$, $R_3$, R'3, $R_4$ and $R'_4$ are each independently S or $NR_a$, with $R_a$ and $R_b$ are each independently H or an alkyl $C_1$-$C_{10}$.

3. A method according to claim 1, wherein in the compound of formula (I):

W, $R_4$ and $R'_4$ are absent,

V represents:

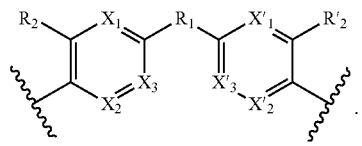

4. A method according to claim 3, wherein compound of formula (I) is selected from the group consisting of:

Y=Y'=CNH$_2$, $R_1$=SO$_2$, $R_2$=R'$_2$=NO$_2$ and $R_3$=R'$_3$=S (1),
Y=Y'=CNH$_2$, $R_1$=SO$_2$, $R_2$=R'$_2$=NO$_2$ and $R_3$=R'$_3$=NH (2),
Y=Y'=N, $R_1$=SO$_2$, $R_2$=R'$_2$=NO$_2$ and $R_3$=R'$_3$=S (3),
Y=Y'=N, $R_1$=SO$_2$, $R_2$=R'$_2$=NO$_2$ and $R_3$=R'$_3$=NH (4),
Y=Y'=N, $R_1$=SO$_2$, $R_2$=R'$_2$=COOR$_a$ and $R_3$=R'$_3$=NH (5),
Y=Y'=N, $R_1$=SO$_2$, $R_2$=R'$_2$=COOR$_a$ and $R_3$=R'$_3$=S (6),
Y=Y'=N, $R_1$=5, $R_2$=R'$_2$=COOR$_a$ and $R_3$=R'$_3$=S (7),
Y=Y'=N, $R_1$=5, $R_2$=R'$_2$=COOR$_a$ and $R_3$=R'$_3$=NH (8),
Y=Y'=CNH$_2$, $R_1$=S, $R_2$=R'$_2$=COOR$_a$ and $R_3$=R'$_3$=NH (9),
Y=Y'=CNH$_2$, $R_1$=S, $R_2$=R'$_2$=COOR$_a$ and $R_3$=R'$_3$=S (10),
Y=Y'=CNH$_2$, $R_1$=S, $R_2$=R'$_2$=CONR$_a$R$_b$ and $R_3$=R'$_3$=S (11),
Y=Y'=CNH$_2$, $R_1$=S, $R_2$=R'$_2$=CONR$_a$R$_b$ and $R_3$=R'$_3$=NH (12),
Y=Y'=CNH$_2$, $R_1$=SO$_2$, $R_2$=R'$_2$=CONR$_a$R$_b$ and $R_3$=R'$_3$=NH (13),
Y=Y'=CNH$_2$, $R_1$=SO$_2$, $R_2$=R'$_2$=CONR$_a$R$_b$ and $R_3$=R'$_3$=S (14),
Y=Y'=N, $R_1$=SO$_2$, $R_2$=R'$_2$=CONR$_a$R$_b$ and $R_3$=R'$_3$=S (15),
Y=Y'=N, $R_1$=SO$_2$, $R_2$=R'$_2$=CONR$_a$R$_b$ and $R_3$=R'$_3$=NH (16),
Y=Y'=CCOOH, $R_1$=SO$_2$, $R_2$=R'$_2$=NO$_2$ and $R_3$=R'$_3$=S (17),
Y=Y'=CCH$_2$PO(OC$_2$H$_5$)$_2$, $R_1$=SO$_2$, $R_2$=R'$_2$=NO$_2$ and $R_3$=R'$_3$=NH (18), and in each compound (1) to (18):

$X_1$ =$X_2$ =$X_3$ =$X'_1$=$X'_2$ =$X'_3$ =$X_4$ =$X_5$ =$X_6$ =$X_7$ =$X'_4$ =$X'_5$ =$X'_6$ =$X'_7$ =CH, $R_a$ and $R_b$ are each independently H or an alkyl $C_1$-$C_{10}$.

5. A method according to claim 1, wherein in the compound of formula (I):

W has the same meaning as V,

V represents:

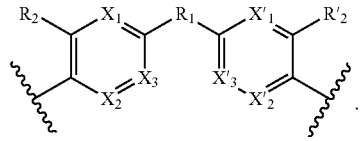

6. A method according to claim 5, wherein compound of formula (I) is selected from the group consisting of:

$R_1$=SO$_2$, $R_2$=R'$_2$=NO$_2$, $R_3$=R'$_3$=$R_4$=R'$_4$=NH (19),
$R_1$=SO$_2$, $R_2$=R'$_2$=NO$_2$, $R_3$=$R_4$=NH, R'$_3$=R'$_4$=S (20),
$R_1$=S, $R_2$=R'$_2$=NO$_2$, $R_3$=R'$_3$=$R_4$=R'$_4$=NH (21),
$R_1$=S, $R_2$=R'$_2$=NO$_2$, $R_3$=$R_4$=NH, R'$_3$=11'$_4$=S (22),
$R_1$=SO$_2$, $R_2$=R'$_2$=NO$_2$, $R_3$=R'$_3$=S, $R_4$=R'$_4$=NH (23),
$R_1$=S, $R_2$=R'$_2$=NO$_2$, $R_3$=R'$_3$=S, $R_4$=R'$_4$=NH (24), and in each compound (19) to (24):

$X_1$ =$X_2$ =$X_3$ =$X'_i$=$X'_2$ =$X'_3$ =$X_4$ =$X_5$ =$X_6$ =$X_7$ =$X'_4$ =$X'_5$ =$X'_6$ =$X'_7$ =CH.

7. A method according to claim 1, wherein in the compound of formula (I):

W, $R_4$ and $R'_4$ are absent,

V represents:

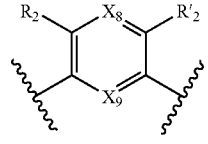

8. A method according to claim 7, wherein compound of formula (I) is selected from the group consisting of:

Y=Y'=N, $R_2$=R'$_2$=NO$_2$ and $R_3$=R'$_3$=S (25),
Y=Y'=CPO(OH)$_2$, $R_2$=R'$_2$=NO$_2$ and $R_3$=R'$_3$=NH (26),
Y=Y'=CCH$_2$PO(OC$_2$H$_5$)$_2$, $R_2$=R'$_2$=NO$_2$, $R_3$=R'$_3$=NH (27),
Y=Y'=CCOOH, $R_2$=R'$_2$=NO$_2$ and $R_3$=R'$_3$=S (28),
Y=Y'=CNH$_2$, $R_2$=R'$_2$=CO$_2$Et, $R_3$=R'$_3$=S (29), Y=Y'=CCOOH, $R_2=R'_2=CO_2Et$, $R_3=R'_3=S$ (30),
and in each compound (25) to (30):
$X_4=X_5=X_6=X_7=X'_4=X'_5=X'_6=X'_7=X_8=X_9=CH$.

9. A method according to claim 1 wherein in the compound of formula (I):
W has the same meaning as V,
V represents:

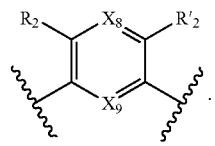

10. A method according to claim 9, wherein compound of formula (I) is selected from the group consisting of:
$R_2=R'_2=NO_2$, $R_3=R'_3=R_4=11'_4=NH$ (31),
$R_2=R'_2=NO_2$, $R_3=R'_3=R_4=R'_4=S$ (32),
$R_2=R'_2=CO_2Et$, $R_3=R'_3=R_4=11'_4=S$ (33),
$R_2=R'_2=NO_2$, $R_3=R'_3=S$, $R_4=R'_4=NH$ (34),
and in each compound (31) to (34):
$X_4=X_5=X_6=X_7=R_4=X'_5=X'_6=X'_7=X_8=X_9=CH$.

11. A method according to claim 1 for the depollution of the air and/or toxic exhaust fumes.

12. Compound having the general formula (I):

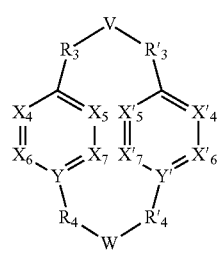

(I)

wherein
V represents:

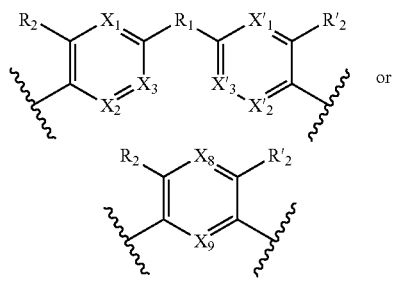

or

W has the same meaning as V or W is absent, and when W is absent then $R_4$ and $R'_4$ are also absent,
$X_1$, $X_2$, $X_3$, $X'_1$, $X'_2$, $X'_3$, $X_4$, $X_5$, $X_6$, $X_7$, $X'_4$, $X'_5$, $X'_6$, $X'_7$, $X_8$ and $X_9$ are each independently N or a CH group,
when W has the same meaning as V, then Y and Y' are each a carbon atom,
when W is absent, then Y and Y' are each independently N or a CR group, with R representing H, $R_a$, $NR_aR_b$, $OR_a$, $SR_a$, $CO_2R_a$, $COR_a$, $CONHR_a$, $CONR_aR_b$, $NHCOR_a$, $SO_2R_a$, $SO_2NHR_a$, $SO_2NR_aR_b$, $PR_aR_b$, $P(O)R_aR_b$, $P(O)(OR_a)(OR_b)$, $CH_2PO(OR_a)(OR_b)$, $COCH_2COR_a$, $CSOR_a$, $CSR_a$, $CSNHR_a$, $CSNR_aR_b$, $NHCSR_a$, $P(S)R_aR_b$, $CSCH_2CSR_a$, $NHCONHR_a$, $NHCSNHR_a$ or a five or six-membered aromatic or heteroaromatic compound chosen from benzene, pyridine, diazine, triazine, tetrazine, pyrrole, thiophene, furan, azole, triazole or tetrazole,
with $R_a$ and $R_b$ being each independently H, OH; an alkyl radical having from 1 to 10 carbon atoms (alkyl $C_1$-$C_{10}$); a five or six-membered carbocycle chosen from cyclohexane, piperidine, piperazine, tetrahydrothiophene, tetrahydropyrrole or dihydroazole; or an aromatic or heteroaromatic compound chosen from pyridine, diazine, triazine, tetrazine, pyrrole, thiophene, furan, azole, triazole, tetrazole, benzoazole, benzotriazole or indole,
$R_1$ represents O, S, $SO_2$, SO, CO, a $NR_a$, $SiR_aR_b$, $SnR_aR_b$, $BR_a$ or a $PR_a$ group, $R_a$ and $R_b$ being as defined above,
$R_2$ and $R'_2$ are each independently $COOR_a$, $NO_2$, $CONR_aR_b$, $SO_2R_a$, $SO_3H$, $OSO_3H$, $COR_a$, $PO_3H_2$, $OPO_3H_2$ or CN, $R_a$ and $R_b$ being as defined above,
$R_3$, $R'_3$, $R_4$ and $R'_4$ are each independently S, $NR_a$, P, Se or Te, $R_a$ being as defined above,
with the proviso that when W, $R_4$, $R'_4$ are absent, and V represents

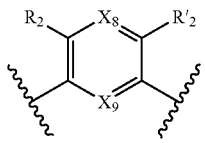

then

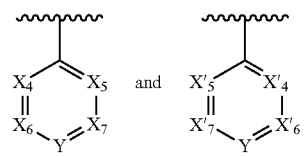

do not represent:

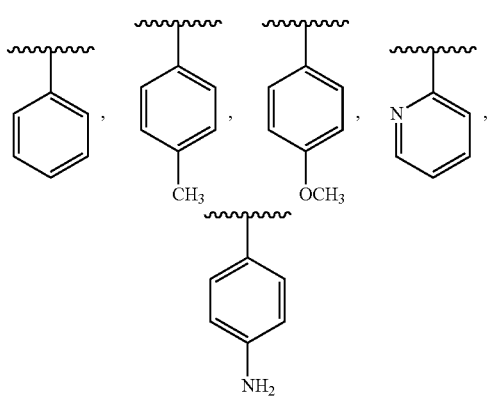

and with the proviso that the above formula (I) does not represent one of the seven following compounds wherein:

W is absent, V represents

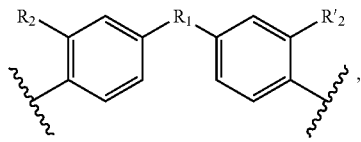, $X_4=X_5=X_6=X_7=X'_4=X'_5=X'_6=X'_7=CH$, and $Y=Y'=CH$, $R_1=SO_2$, $R_2=R'_2=NO_2$, $R_3=R'_3=NH$;
W is absent, V represents

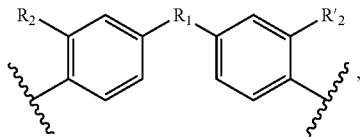, $X_4=X_5=X_6=X_7=X'_4=X'_5=X'_6=X'_7=CH$, and $Y=Y'=CNH_2$, $R_1=SO_2$, $R_2=R'_2=SO_3H$, $R_3=11'_3=S$;
W is absent, V represents

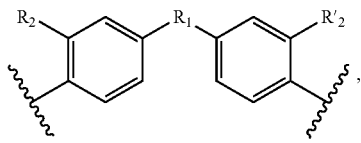, $X_4=X_5=X_6=X_7=X'_4=X'_5=X'_6=X'_7=CH$, and $Y=Y'=CNH_2$; $R_1=CO$; $R_2=R'_2=SO_3H$, $R_3=11'_3=S$;
W is absent, V represents

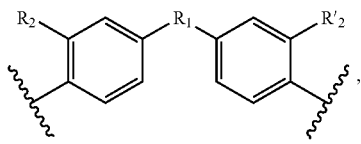, $X_4=X_5=X_6=X_7=X'_4=X'_5=X'_6=X'_7=CH$, and $Y=Y'=CH$, $R_1=SO_2$; $R_2=R'_2=NO_2$, $R_3=R'_3=S$;

$-W=V=$ 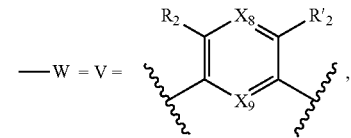, $X_4=X_5=X_6=X_7=X'_4=X'_5=X'_6=X'_7=CH$, and $Y=Y'C—$, $R_3=R'_3=R_4=R'_4=S$, $R_2=R'_2=NO_2$, $X_8=X_9=CH$;

$-W=V=$ 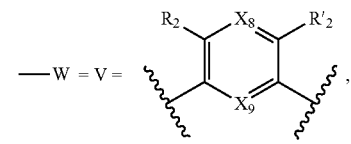, $X_4=X_5=X_6=X_7=X'_4=X'_5=X'_6=X'_7=CH$, and $Y=Y'C—$, $R_3=R'_3=R_4=R'_4=NH$, $R_2=R'_2=NO_2$, $X_8=X_9=CH$;

$-W=V=$ 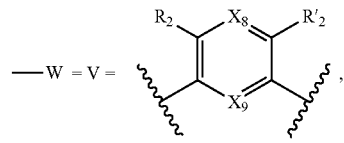, $X_4=X_5=X_6=X_7=X'_4=X'_5=X'_6=X'_7=CH$, and $Y=Y'C—$, $R_3=R'_3=R_4=R'_4=NCH_3$, $R_2=R'_2=NO_2$, $X_8=X_9=CH$.

13. Compound according to claim 12, wherein in the compound of formula (I):
V represents:

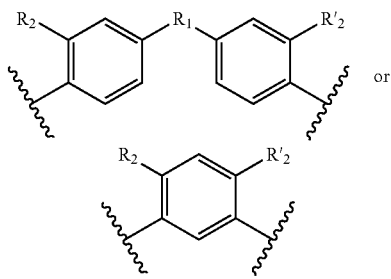

$X_4$, $X_5$, $X_6$, $X_7$, $X'_4$, $X'_5$, $X'_6$ and $X'_7$ are each independently N or CH,
when W has the same meaning as V, then Y and Y' are each a carbon atom,
when W is absent, then Y and Y' are each independently N or a CR group, R being H, $NR_aR_b$, $CO_2R_a$, $P(O)(OR_a)(OR_b)$, $CH_2PO(OR_a)(OR_b)$,
$R_1$ represents S, $SO_2$, $NR_a$ or O,
$R_2$ and $R'_2$ are each independently $NO_2$, $COOR_a$, $COR_a$ or $CONR_aR_b$,
$R_3$, $R'_3$, $R_4$ and $R'_4$ are each independently S or $NR_a$,
with $R_a$ and $R_b$ are each independently H or an alkyl $C_1$-$C_{10}$.

14. Compound of formula (I) according to claim 12, wherein in the compound of formula (I):
W, $R_4$ and $R'_4$ are absent,
V represents:

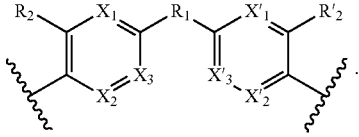

15. Compound according to claim 14, which is selected from the group consisting of compounds of formula (I) wherein:
$Y=Y'=CNH_2$, $R_1=SO_2$, $R_2=R'_2=NO_2$ and $R_3=R'_3=S$ (1),
$Y=Y'=CNH_2$, $R_1=SO_2$, $R_2=R'_2=NO_2$ and $R_3=R'_3=NH$ (2),
$Y=Y'=N$, $R_1=SO_2$, $R_2=R'_2=NO_2$ and $R_3=R'_3=S$ (3), $Y=Y'=N$, $R_1=SO_2$, $R_2=R'_2=NO_2$ and $R_3=R'_3=NH$ (4), $Y=Y'=N$, $R_1=SO_2$, $R_2=R'_2=COOR_a$ and $R_3=R'_3=NH$ (5), $Y=Y'=N$, $R_1=SO_2$, $R_2=R'_2=COOR_a$ and $R_3=R'_3=S$ (6), $Y=Y'=N$, $R_1=S$, $R_2=R'_2=COOR_a$ and $R_3=R'_3=S$ (7), $Y=Y'=N$, $R_1=S$, $R_2=R'_2=COOR_a$ and $R_3=R'3=NH$ (8), $Y=Y'=CNH_2$, $R_1=S$, $R_2=R'_2=COOR_a$ and $R_3=R'_3=NH$ (9), $Y=Y'=CNH_2$, $R_1=S$, $R_2=R'_2=COOR_a$ and $R_3=R'_3=S$ (10), $Y=Y'=CNH_2$, $R_1=S$, $R_2=R'_2=CONR_aR_b$ and $R_3=R'_3=S$ (11), $Y=Y'=CNH_2$, $R_1=S$, $R_2=R'_2=CONR_aR_b$ and $R_3=R'_3=NH$ (12), $Y=Y'=CNH_2$, $R_1=SO_2$, $R_2=R'_2=CONR_aR_b$ and $R_3=R'_3=NH$ (13), $Y=Y'=CNH_2$, $R_1=SO_2$, $R_2=R'_2=CONR_aR_b$ and $R_3=R'_3=S$ (14), $Y=Y'=N$, $R_1=SO_2$, $R_2=R'_2=CONR_aR_b$ and $R_3=R'_3=S$ (15), $Y=Y'=N$, $R_1=SO_2$, $R_2=R'_2=CONR_aR_b$ and $R_3=R'_3=NH$ (16), $Y=Y'=CCOOH$, $R_1=SO_2$, $R_2=R'_2=NO_2$ and $R_3=R'_3=S$ (17), $Y=Y'=CCH_2PO(OC_2H_5)_2$, $R_1=SO_2$, $R_2=R'_2=NO_2$ and $R_3=R'_3=NH$ (18), and in each compound (1) to (18):
$X_1=X_2=X_3=X'_1=X'_2=X'_3=X_4=X_5=X_6=X_7=X'_4=X'_5=X'_6=X'_7=CH$, $R_a$ and $R_b$ are each independently H or an alkyl $C_1$-$C_{10}$.

16. Compound of formula (I) according to claim 12, wherein:
W has the same meaning as V,
V represents:

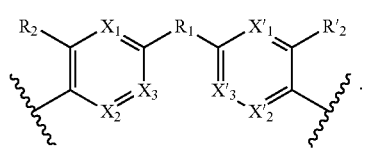

17. Compound according to claim 16, which is selected from the group consisting of compounds of formula (I) wherein:

$R_1=SO_2$, $R_2=R'_2=NO_2$, $R_3=R'_3=R_4=R'_4=NH$ (19),
$R_1=SO_2$, $R_2=R'_2=NO_2$, $R_3=R_4=NH$, $R'_3=R'_4=S$ (20),
$R_1=S$, $R_2=R'_2=NO_2$, $R_3=R'_3=R_4=R'_4=NH$ (21),
$R_1=S$, $R_2=R'_2=NO_2$, $R_3=R_4=NH$, $R'_3=11'_4=S$ (22),
$R_1=SO_2$, $R_2=R'_2=NO_2$, $R_3=R'_3=S$, $R_4=R'4=NH$ (23),
$R_1=S$, $R_2=R'_2=NO_2$, $R_3=R'_3=S$, $R_4=R'_4=NH$ (24), and in each compound (19) to (24):
$X_1=X_2=X_3=X'i=X'_2=X'_3=X_4=X_5=X_6=X_7=X'_4=X'_5=X'_6=X'_7=CH$.

18. Compound of formula (I) according to claim 12, wherein:
W, $R_4$ and $R'_4$ are absent,
V represents:

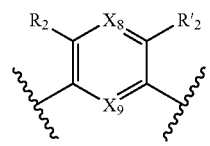

19. Compound according to claim 18, which is selected from the group consisting of compounds of formula (I) wherein:

$Y=Y'=N$, $R_2=R'_2=NO_2$ and $R_3=R'_3=S$ (25),
$Y=Y'=CPO(OH)_2$, $R_2=R'_2=NO_2$ and $R_3=R'_3=NH$ (26),
$Y=Y'=CCH_2PO(OC_2H_5)_2$, $R_2=R'_2=NO_2$, $R_3=R'_3=NH$ (27),
$Y=Y'=CCOOH$, $R_2=R'_2=NO_2$, $R_3=R'_3=S$ (28),
$Y=Y'=CNH_2$, $R_2=R'_2=CO_2Et$, $R_3=R'_3=S$ (29),
$Y=Y'=CCOOH$, $R_2=R'_2=CO_2Et$, $R_3=R'_3=S$ (30), and in each compound (25) to (30):
$X_4=X_5=X_6=X_7=X'_4=X'_5=X'_6=X'_7=X_8=X_9=CH$.

20. Compound of formula (I) according claim 12, wherein:
W has the same meaning as V,
V represents:

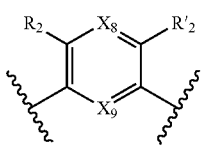

21. Compound according to claim 20, which is selected from the group consisting of compounds of formula (I) wherein:

$R_2=R'_2=CO_2Et$, $R_3=R'_3=R_4=R'_4=S$ (33),
$R_2=R'_2=NO_2$, $R_3=R'_3=S$, $R_4=R'_4=NH$ (34), and in each compound (33) to (34):
$X_4=X_5=X_6=X_7=X'_4=X'_5=X'_6=X'_7=X_8=X_9=CH$.

22. A method according to claim 1, wherein the polluting gases are those selected from the group comprising carbon dioxide, methane, sulfur dioxide, nitrogen oxides, carbon monoxide, linear hydrocarbons, linear mono-olefins and their mixtures.

* * * * *